US010524471B2

(12) United States Patent
Hirt et al.

(10) Patent No.: US 10,524,471 B2
(45) Date of Patent: Jan. 7, 2020

(54) COMPOSITIONS AND METHODS FOR INCREASING SALT TOLERANCE IN PLANTS

(71) Applicant: King Abdullah University of Science and Technology, Thuwal (SA)

(72) Inventors: Heribert Hirt, Thuwal (SA); Axel de Zelicourt, Thuwal (SA); Maged Saad, Thuwal (SA)

(73) Assignee: King Abdullah University of Science and Technology, Thuwai (SA)

( * ) Notice: Subject to any disclaimer, the term of this patent is extended or adjusted under 35 U.S.C. 154(b) by 0 days.

(21) Appl. No.: 16/048,142

(22) Filed: Jul. 27, 2018

(65) Prior Publication Data

US 2018/0338493 A1    Nov. 29, 2018

Related U.S. Application Data

(63) Continuation-in-part of application No. 16/072,137, filed as application No. PCT/IB2017/050314 on Jan. 20, 2017.

(60) Provisional application No. 62/630,013, filed on Feb. 13, 2018, provisional application No. 62/281,404, filed on Jan. 21, 2016.

(51) Int. Cl.
*A01N 25/02* (2006.01)
*A01N 37/42* (2006.01)
*A01N 63/00* (2006.01)

(52) U.S. Cl.
CPC ............. *A01N 37/42* (2013.01); *A01N 25/02* (2013.01); *A01N 63/00* (2013.01)

(58) Field of Classification Search
None
See application file for complete search history.

(56) References Cited

U.S. PATENT DOCUMENTS

2015/0373993 A1    12/2015  Von Maltzahn

FOREIGN PATENT DOCUMENTS

| CA | 2953466 | | 12/2015 |
| JP | 51446766 | * | 11/1979 |
| JP | 5702081 | * | 4/1982 |
| WO | 2015091967 | | 6/2015 |
| WO | 2017125894 | | 7/2017 |

OTHER PUBLICATIONS

Sunaina et al.(Bacterial Metabolites from Bacillus Cereus B4 Responsible for Potato Plant Growth(Potato J. 32(3-4): 167-188, 2005). (Year: 2005).*
Arshad et al., Kinetics and effects of trace elements and electron complexes on 2-keto-4-methylthiobutyric acid-dependent biosynthesis of ethylene in soil, Letters in Applied Microbiology (2004), vol. 39, No. 3, pp. 306-309, 20 refs. (Year: 2004).*
Martensson, J., The occurrence of 4-methylthio-2-hydroxybutyrate in human urine, Analytical Biochemistry, (1986) vol. 154, No. 1, pp. 43-49. (Year: 1986).*
Andres-Barrao, et al., "Complete Genome Sequence Analysis of *Enterobacter* sp. SA187, a Plant Multi-Stress Tolerance Promoting Endophytic Bacterium", Front Microbiol, 8:1-21 (2017).
Bolger, et al., "Trimmomatic: a flexible trimmer for Illumina sequence data", Bioinformatics, 30:2114-2120 (2014).
Chen, et al. "Application of Plant growth-promoting endophytes (PGPE) isolated from *Solanum nugrum* L. for phytoextraction of Cd-polluted soils", Apl. Soil Ecol., 46(3):383-389 (2010).
Coleman-Derr, et al., "Building the crops of tomorrow: advantages of symbiont-based approaches to improving abiotic stress tolerance", Front Microbiol., 5:283 (2014).
de Zelicourt, "Rhizosphere microbes as essential partners for plant stress tolerance", et al., Mol Plant, 6:242-245 (2013)).
Deinlein, et al., "Plant salt-tolerance mechanisms", Trends Plant Sci, 19:371-379 (2014).
Eckert, et al., "Ethylene-forming enzyme and bioethylene production", Biotechnol Biofuels, 7:33 (2014).
Gao, et al., "Symbiotic adaptation drives genome streamlining of the cyanobacterial sponge symbiont *Candidatus Synechococcus spongiarum*", MBio, 5(2)e0079-14, (2014).
Glick, et al., "Plant Growth-Promoting Bacteria: Mechanisms and Applications", Scientifica, 2012:1-15 (2012).
Guzmán, et al., "Exploiting the triple response of *Arabidopsis* to identify ethylene-related mutants", Plant Cell, 2:513-523 (1990).
Han, et al., "Beneficial soil bacterium *Bacillus subtilis* (GB03) augments salt tolerance of white clover", Front Plant Sci, 5:525 (2014).
Hanin et al., "New Insights on Plant Salt Tolerance Mechanisms and Their Potential Use for Breeding", Front Plant Sci., 7:1-17 (2016).
Hossain, et al., "One-step biosynthesis of α-keto-γ-methylthiobutyric acid from L-methionine by an *Escherichia coli* whole-cell biocatalyst expressing an engineered L-amino acid deaminase from Proteus vulgaris", PLOS One, 9(12):e114291 (2014).
Kaplan, et al., "A survey of the microbial community in the rhizosphere of two dominant shrubs of the Negev Desert highlands, *Zygophyllum dumosum* (*Zygophyllaceae*) and *Atriplex halimus* (*Amaranthaceae*), using cultivation-dependent and cultivation-independent methods", Am J Bot, 100:1713-1725 (2013).
Karlidag, et al., "Plant Growth-promoting Rhizobacteria Mitigate Deleterious Effects of Salt Stress on Strawberry Plants (*Fragaria ×ananassa*)", Hortic Sci, 48:563-567 (2013).
Konishi and Yanagisawa, ",Ethylene signaling in *Arabidopsis* involves feedback regulation via the elaborate control of EBF2 expression by EIN3", Plant J, 55:821-831 (2008).

(Continued)

Primary Examiner — Alton N Pryor
(74) Attorney, Agent, or Firm — Pabst Patent Group LLP

(57) ABSTRACT

Methods and compositions for increasing tolerance to abiotic stresses in plants are provided. One embodiment provides a method for increasing salt tolerance in a plant by treating the plant with an amount of 2-keto-4-methylthio-butyric acid (KMBA) effective to increase salt tolerance in the plant relative to an untreated plant. Typically KMBA is in an aqueous solution used to irrigate the plant, seed, or seedling. In a preferred embodiment, the aqueous solution is a salt solution, including but not limited to seawater. The KMBA is typically present in the aqueous solution at 1.0 to 250 nM, preferably at least 100 nM.

26 Claims, 13 Drawing Sheets

Specification includes a Sequence Listing.

(56) References Cited

OTHER PUBLICATIONS

Lafi, et al., "Draft Genome Sequence of the Plant Growth—Promoting Rhizobacterium Acinetobacter radioresistens Strain SA188 Isolated from the Desert Plant *Indigofera argentea*", Genome Announc, 9-10 (2017).

Marasco, et al., "A drought resistance-promoting microbiome is selected by root system under desert farming", PLoS One, 7:e48479 (2012).

Nadeem, et al., "Variation in growth and ion uptake of maize due to inoculation with plant growth promoting rhizobacteria under salt stress", Microbiology, 25:78-84 (2006).

Negrao et al., "Evaluating physiological responses of plants to salinity stress", Ann Bot, 119:1-11 (2017).

Park et al., "Abscisic acid inhibits type 2C protein phosphatases via the PYR/PYL family of START proteins", Science, 324:1068-1071 (2009).

Rifat, et al., "Soil beneficial bacteria and their role in plant growth promotion: a review", Annals of Microbiol., 60(4):579-598 (2010).

Schwartz, et al., "Biochemical characterization of the aba2 and aba3 mutants in *Arabidopsis thaliana*", Plant Physiol, 114 :161-166 (1997).

Shabala, et al., "Learning from halophytes: physiological basis and strategies to improve abiotic stress tolerance in crops", Ann Bot, 112:1209-1221 (2013).

Staswick, et al., "Methyl jasmonate inhibition of root growth and induction of a leaf protein are decreased in an *Arabidopsis thaliana* mutant", Proc Natl Acad Sci USA, 89 :6837-6840 (1992).

Sun, et al., "Potassium Retention under Salt Stress Is Associated with Natural Variation in Salinity Tolerance among *Arabidopsis Accessions*", PLoS One, 10:e0124032 (2015).

Trapnell, et al., "Transcript assembly and quantification by RNA-Seq reveals unannotated transcripts and isoform switching during cell differentiation", Nat Biotechnol, 28:511-515 (2010).

Zhang, et al., "Soil bacteria confer plant salt tolerance by tissue-specific regulation of the sodium transporter HKT1", Mol Plant-Microbe Interact, 21:737-744 (2008).

\* cited by examiner

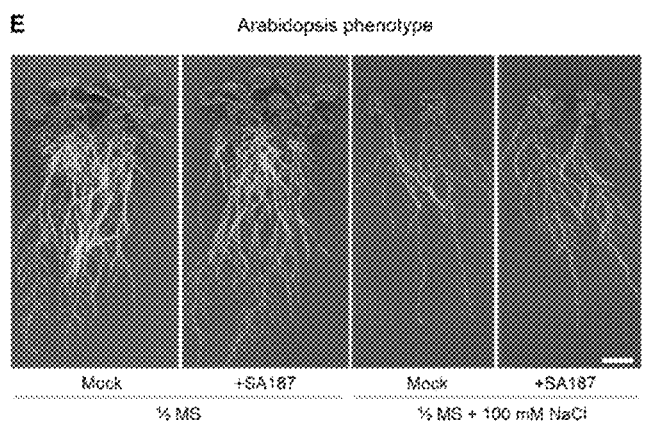
FIG. 2E
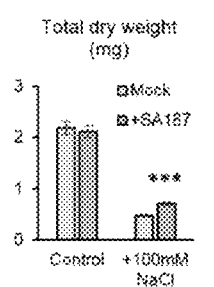 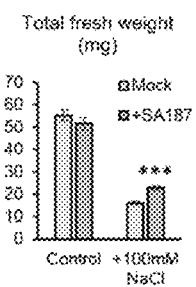 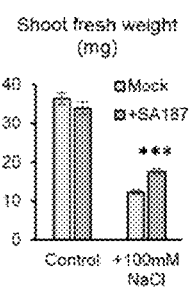 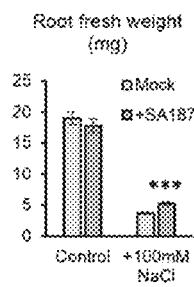 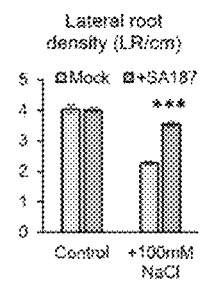
FIG. 2F　　FIG. 2G　　FIG. 2H　　FIG. 2I　　FIG. 2J

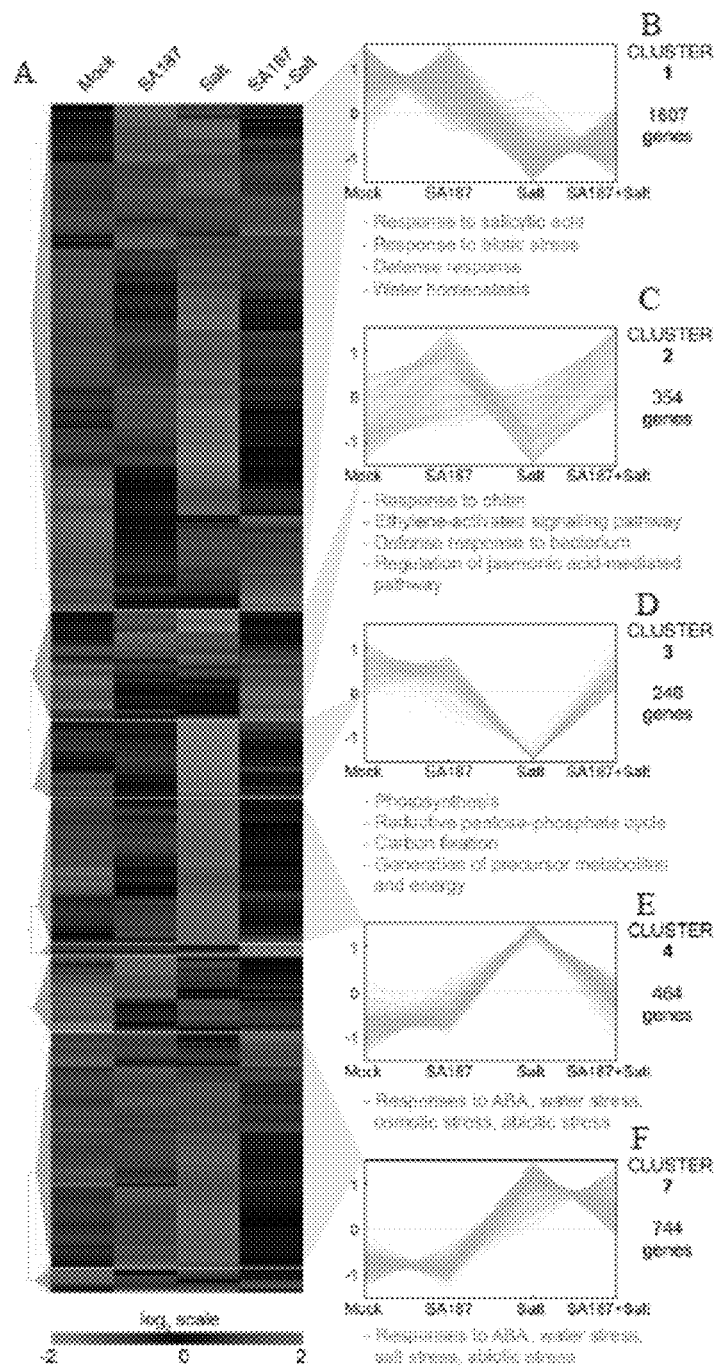
FIG. 4A-F

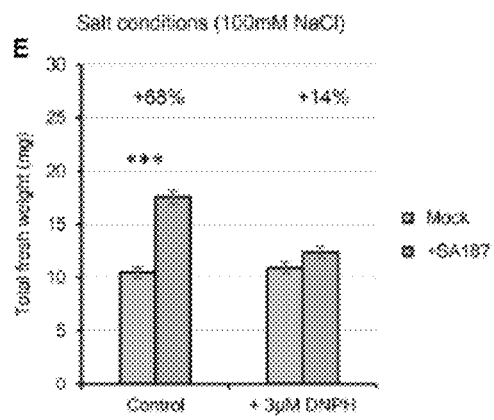
FIG. 7E
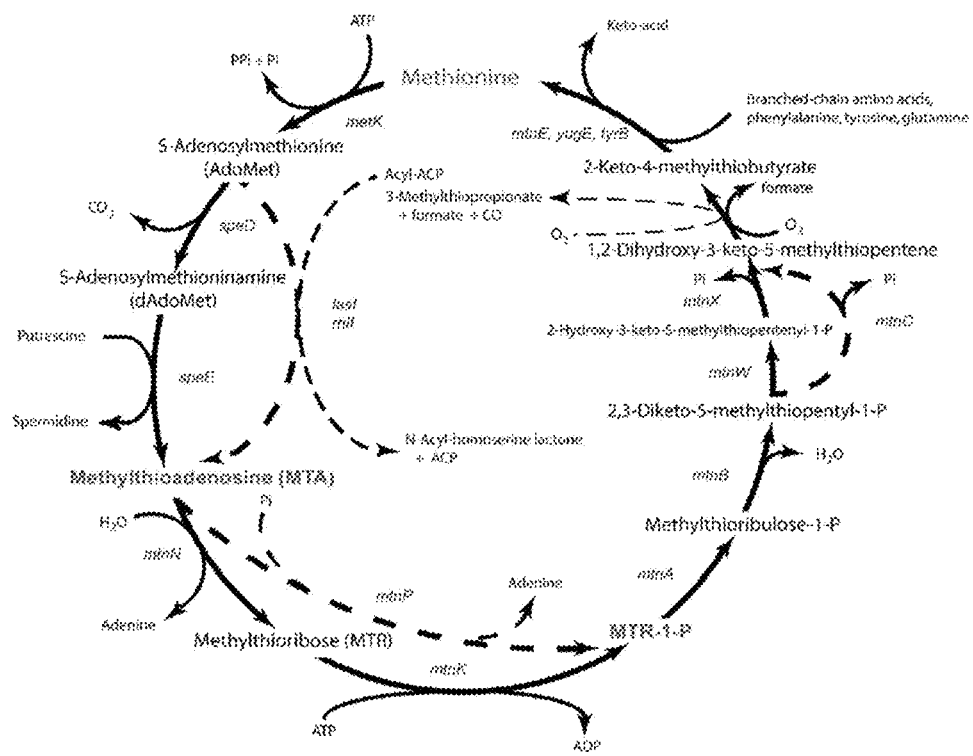
FIG. 7F (adapted from Sekowsak et al., BMC Microbiol., 4:9 (2004)

COMPOSITIONS AND METHODS FOR INCREASING SALT TOLERANCE IN PLANTS

CROSS-REFERENCE TO RELATED APPLICATIONS

This application claims the benefit and priority of U.S. Provisional Patent Application No. 62/630,013 filed on Feb. 13, 2018, and is a continuation-in part of U.S. Ser. No. 16/072,137 filed on Jul. 23, 2018, which is a National Phase application under 35 U.S.C. § 371 of International Application No. PCT/IB2017/050314, filed on Jan. 20, 2017, entitled "COMPOSITIONS AND METHODS FOR PROVIDING PLANTS WITH TOLERANCE TO ABIOTIC STRESS CONDITIONS", which claims benefit of and priority to U.S. Provisional Patent Application No. 62/281,404 filed on Jan. 21, 2016, and are incorporated herein in their entirety.

FIELD OF THE INVENTION

The invention is generally directed to plant cultivation under abiotic stress conditions.

REFERENCE TO SEQUENCE LISTING

The Sequence Listing submitted Jul. 27, 2018, as a text file named "KAUST_2018_114_02_ST25.txt" created on Jul. 27, 2018, and having a size of 5,507,846 bytes is hereby incorporated by reference pursuant to 37 C.F.R. § 1.52(e)(5).

BACKGROUND OF THE INVENTION

Plants as sessile organisms are facing multiple stresses during their lifetime. Among them, abiotic stresses, such as salt stress, can cause severe crop yield reduction, leading to food security issues in many regions of the world. In order to respond to growing food demands, especially in the context of global climate change and an increasing world population, it then becomes urgent to develop new strategies to generate more tolerant crops to abiotic stresses.

Therefore it is an object of the invention to provide compositions and methods for increasing tolerance in plants to abiotic stresses.

It is another object of the invention to provide seed coating compositions that provide plants with resistance or tolerance to abiotic stress conditions.

It is still another object to provide methods for growing plants under abiotic stress conditions.

SUMMARY OF THE INVENTION

Methods and compositions for increasing tolerance to abiotic stresses in plants are provided. The methods include providing the plant with 2-keto-4-methylthiobutyric acid (KMBA) exogenously ("exogenous KMBA method), alone or in combination with modifying the plant with a microbial system that results in production of KMBA in the plant ("endogenous KMBA method"). The exogenous KMBA method include treating seeds, seedlings or mature plants with 2-keto-4-methylthiobutyric acid (KMBA). The exogenous KMBA method in one increases salt tolerance in a plant by treating the plant with an amount of KMBA) effective to increase salt tolerance in the plant relative to an untreated plant. Typically KMBA is in an aqueous solution used to irrigate the plant, seed, or seedling. In a preferred embodiment, the aqueous solution is a salt solution, including but not limited to seawater. The KMBA is typically present in the aqueous solution at 1.0 to 250 nM, preferably at least 100 nM.

Another embodiment provides cultivating a plant in sodic soil by irrigating the plant, seed, or seedling in the sodic soil with a aqueous solution containing 1.0 to 250 nM KMBA. The aqueous solution is typically water. The water can be rainwater, wellwater, or water from natural sources such as rain, lakes, glaciers, rivers, and streams.

When KMBA is combined with a salt solution, the salt is can be from 1.0 to 10% (w/v) salt. In a preferred embodiment, the salt solution is about 3.5% salt. The salt solution can contain salts of sodium, chloride, sulfates, magnesium, calcium, potassium, and combinations thereof.

Another embodiment provides a method for cultivating a plant by planting seeds or seedlings of the plant and irrigating the seeds or seedlings with a saline solution comprising KMBA. The plant can be an agricultural crop plant or a forage crop plant. Representative plants include but are not limited to rice, wheat, sugarcane, maize, soybean, cotton, vegetables, rape, mustard, sorghum, millet, grass, *Brassica* spp., rapeseed, barley, hay, and alfalfa.

Still another embodiment provides a method of increasing tolerance to abiotic stress in a plant by treating the plant with a composition containing an effective amount of KMBA to increase tolerance to the abiotic stress. In certain embodiments, the abiotic stress is due to water salinity, soil salinity, or both. The KMBA can be present at a concentration of 1.0 to 250 nM, preferably 100 nM Yet another embodiment provides an irrigation solution containing 1.0 to 250 nM KMBA in an aqueous saline solution. The aqueous saline solution typically contains 1 to 10% salt (w/v). The aqueous solution is preferably seawater.

The endgenous KMBA method providing seeds, seedlings or mature plants with a microbial system that results in production of KMBA in mature plants. In some embodiments, seeds or plant roots can be inoculated with or coated with a microbial system that results in production of KMBA in mature plants. A preferred microbial system *Enterobacter* sp. SA187. In other embodiments, seeds, seedling and plants can be grown using substrates containing an effective amount of *Enterobacter* sp. SA187 to inhibit or reduce abiotic stress in the plant. Suitable plant substrates include, but are not limited to soil, peat, compost, vermiculite, perlite, sand, clay and combinations thereof.

Another embodiment provides a bacterium genetically engineered to express KMBA or increased levels of KMBA relative to an unmodified bacterium, which can be used as a a microbial system that results in production of KMBA in mature plants. In a preferred embodiment the bacterium is an endophytic bacterium. The engineered bacterium can be used to inoculate plants and increase tolerance in the plant to abiotic stress conditions.

BRIEF DESCRIPTION OF THE DRAWINGS

FIGS. 1A and 1D are bar graphs showing plant height (cm) of alfalfa plants inoculated with mock (gray bar) and SA187 (green bar) and subjected to low or high saline conditions. FIGS. 1B and 1E are bar graphs showing fresh weight (tons/ha) of alfalfa plants inoculated with mock (gray bar) and SA187 (green bar) and subjected to low or high saline conditions. FIGS. 1C and 1F are bar graphs showing dry weight (tons/ha) of alfalfa plants inoculated with mock (gray bar) and SA187 (green bar) and subjected to low and high saline conditions. Data from the first season (FIGS. 1A, 1B, 1C) and second season (FIGS. 1D, 1E, 1F) are displayed; each column represents a mean of 3 harvests from 4 experimental plots error bars are SE. An increase of each parameter for SA187-treated plants related to Mock is indicated in %. Asterisks indicate a statistical difference (* P<0.05;  P<0.01, * P<0.001).

FIGS. 2A-2J show that SA187 enhances *Arabidopsis* tolerance to salt stress. FIG. 2A is a bar graph that shows germination efficiency on ½ MS medium without (mock) or with SA187 (+SA187) (n>300, 3 biological replicates, bars represent SE). FIG. 2B is a bar graph that shows average root hair length (μm) of 10% longest root hairs (n>70) in 5-day-old seedlings grown vertically on ½ MS medium without (mock) or with SA187. Error bars represent SE. FIG. 2C is a representative image showing typical root hair morphology of 5-day-old seedlings used for the analysis in FIG. 2B. Scale bar represents 200 μm. FIG. 2D is a line graph showing root length (cm) over time in SA187-inoculated (upper solid line) or mock-treated (lower solid line) *Arabidopsis* seedlings after transfer of 5-day-old seedlings from ½ MS to ½ MS with or without 100 mM NaCl (dashed lines) (n=60). Error bars represent SE. FIG. 2E are representative images of SA187-colonized 17-day-old plants showing enhanced growth under salt stress (½ MS+100 mM NaCl) but negligible differences under normal conditions (½ MS). Scale bar represents 1 cm. FIGS. 2F-2J are bar graphs showing (FIG. 2F) total plant dry weight (mg), (FIG. 2G) total plant fresh weight (mg), (FIG. 2H) shoot fresh weight (mg), and (I) root fresh weight (mg) of 17-day-old seedlings and (FIG. 2J) lateral root density of 13-day-old seedlings inoculated by SA187 (green bar) or mock-treated (gray bar) transferred 5 days after germination from ½ MS to ½ MS with or without 100 mM NaCl. All plots represent the mean of three biological replicates (n>39). Error bars represent SE. Asterisks indicate a statistical difference based on the Student t-test (* P<0.05;  P<0.01; * P<0.001).

FIGS. 3A-3C are bar graphs showing (FIG. 3A) shoot Na+ content, (FIG. 3B) shoot K+ content, and (FIG. 3C) shoot Na+/K+ ratio of 17-day-old mock- (gray bar) or SA187- (green bar) inoculated *Arabidopsis* seedlings exposed for 12 days to ½ MS with or without 100 mM NaCl {48>n>36}. FIGS. 3D-3F are bar graphs showing (FIG. 3D) root Na+ content, (FIG. 3E) root K+ content, and (FIG. 3F) root Na+/K+ ratio of 17-day-old mock- (gray bar) or SA187- (green bar) inoculated *Arabidopsis* seedlings exposed for 12 days to ½ MS with or without 100 mM NaCl (48>n>12). All plots represent the mean of three biological replicates, and error bars represent SE. Asterisks indicate a statistical difference based on Mann-Whitney test (* P<0.05;  P<0.01, * P<0.001).

FIGS. 4A-4F shows transcriptome analysis of *Arabidopsis* response to SA187. FIG. 4A is a heat map showing response of genes in *Arabidopsis* seedlings in response to SA187, salt (100 mM NaCl) or both treatments based on the RNA-Seq analysis. Heat map colors indicate expression levels. FIGS. 4B-4F are hierarchical clustering of up- and down-regulated genes from the RNA-Seq analysis. For every gene, FPKM values were normalized. For the most relevant clusters, gene families significantly enriched are indicated based on gene ontology.

FIGS. 7D and 7E are bar graphs showing total fresh weight of mock- (gray bars) and SA187- (green bars) inoculated 17-day-old *Arabidopsis* seedlings grown on ½ MS medium (FIG. 7D) or ½ MS with 100 mM NaCl (FIG. 7E) supplemented with 3 μM DNPH. All plots represent the mean of four biological replicates (n>75). Error bars representing SE, beneficial index(%) is displayed above. Asterisks indicate a statistical difference based on Student t-test (*** P<0.001). FIG. 7F shows the methionine salvage pathway.

DETAILED DESCRIPTION OF THE INVENTION

I. Definitions

Figure 1A:
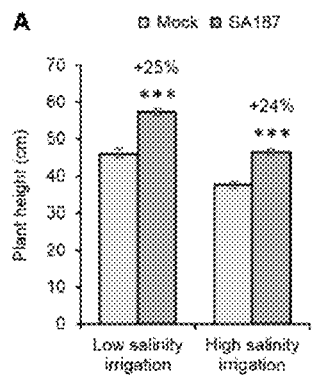
FIGS. 1A-1F show growth parameters of alfalfa in field trials.
Figure 1B:
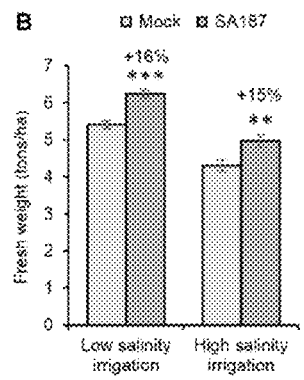
Figure 1C:
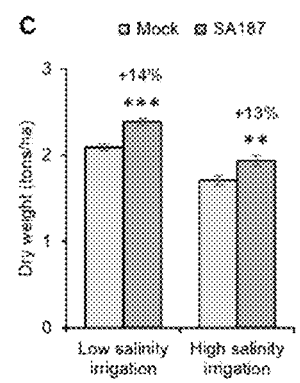

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "plant" refers to the entire plant, seeds of the plant, and seedlings of the plant.

As used herein, "abiotic stress" refers to negative impact of non-living factors on living organisms within the specific environment of the organism. Exemplary abiotic stress conditions include, but are not limited to drought, high heat, high salt, bright light, ultraviolet light, too high and too low temperatures, freezing, heavy metals and hypoxia. Abiotic stresses like salinity, drought or heat negatively affect plant growth and yield and belong to the most limiting factors of agriculture worldwide (Wang et al., *Planta*, 218:1-14 (2003); Zurbriggen et al., *Biotechnol Genet Eng Rev*, 27:33-56 (2010)). For example, salinity, known to affect almost one fourth of arable land globally, is a two-phase stress composed of a rapid osmotic stress and a slower toxic one, resulting from $Na^+$ ions accumulation and loss of $K^+$ in photosynthetic tissues (Negrao et al., *Ann Bot*, 119:1-11 (2017)). Salt stress reduces the rate of photosynthesis, leading to a decrease of plant growth and crop yield (Hanin et al., *Front Plant Sci.*, 7:1-17 (2016)). However, in the context of global climate change and an increasing world population, abiotic stress tolerant crops and sustainable solutions in agriculture are urgently needed to respond to growing food demands (Coleman-Derr, et al., *Front Microbiol.*, 5:283 (2014)).

The effect of salinity on plants includes two components: an osmotic component, being the consequence of an altered osmotic pressure due to an increased salt concentration, and a toxic ion effect as a result of the high $Na^+$ concentration in the shoot (Munns, et al., *Annu Rev Plant Biol*, 59:651-681 (2008); Shabala, et al., *Ann Bot*, 112:1209-1221 (2013)). The toxic effects of $Na^+$ accumulation result in premature senescence, leading to a decrease in photosynthesis efficiency and impaired metabolic processes. $Na^+$ also competes with $K^+$ in membrane transport and enzymatic functions, reducing plant growth. Most plant cells possess mechanisms to counteract the harmful effects of $Na^+$ accumulation by retaining $K^+$ and actively excluding $Na^+$ in roots and/or sequestering $Na^+$ in vacuoles in shoots (Munns, et al., *Annu Rev Plant Biol*, 59:651-681 (2008); Shabala, et al., *Ann Bot*, 112:1209-1221 (2013); Deinlein, et al., *Trends Plant Sci*, 19:371-379 (2014); Sun et al., *PLoS One*, 10:e0124032 (2015)).

Arid regions cover about one quarter of the Earth's land surface and encompass many of the challenges for increasing agricultural productivity (Ezcurra, *UNEP/Earthprint* (2012)). In contrast to better known dryland farming, desert agriculture can function only when crop plants are under irrigation—usually with underground water with various levels of salinity (Cresswell, et al., *Echo* (1998)). Those areas face extreme environmental conditions, characterized by high levels of radiation, low rainfall, extreme temperatures, coarse soil which retains very little moisture, as well as low nutrients and typically high salinity, which all strongly limit the yield of crops (Rewald, et al., *Wallingford: CARI*, 196-218 (2012)). Although deserts appear to be hardly inhabitable, a wide diversity of organisms has adapted to these extreme conditions. Plants along with their interacting microbial partners have evolved sophisticated mechanisms such as production of osmoprotectants, Reactive Oxygen Species scavengers or Late Embryogenesis Abundant proteins to monitor the environment and reprogram their metabolism and development (Chaves, et al., *Ann Bot*, 89:907-916 (2002); Lebre, et al., *Nat Rev Microbiol*, 15:285-296 (2017)). Therefore, this particular environment is an ideal reservoir to isolate and identify beneficial bacteria enhancing plant tolerance towards environmental stresses such as drought, heat or salinity (de Zelicourt, et al., *Mol Plant*, 6:242-245 (2013)).

As used herein, "plant growth promoting bacteria (PGPB)" refers to beneficial bacteria that promote plant growth. PGPB can establish symbiotic associations with plants and promote plant growth under optimal growth conditions or in response to biotic and abiotic stresses (Obledo, et al., *Plant Cell Tissue Organ Cult*, 74:237-241 (2003); Marasco, et al.,*PLoS One*, 7:e48479 (2012); Kaplan, et al., *Am J Bot*, 100:1713-1725 (2013); Mengual, et al., *J Environ Manage*, 134:1-7 (2014); Cherif, et at, *Environ Microbiol Rep*, 7:668-678 (2015); Pieterse, et al., *Annu Rev Phytopathol*, 52:347-375 (2014)). Direct plant growth-promotion mechanisms include the acquisition of nutrients by nitrogen fixation, phosphate and zinc solubilization, or siderophore production for sequestering iron. The modulation of phytohormone levels, such as auxin, ethylene, cytokinin or gibberellin, also largely contributes to the beneficial properties of PGPB (Persello-Cartieaux, et at, *Plant, Cell, Environ*, 26:189-199 (2003); Vessey, *Plant Soil*, 255:571-586 (2003); Hardoim, et al., *Trends Microbiol*, 16:463-471 (2008)). Indirect mechanisms comprise the production of antimicrobial agents against plant pathogenic bacteria or fungi, or inducing systemic resistance against soil-borne pathogens (Pieterse, et al., *Annu Rev Phytopathol*, 52:347-375 (2014); Glick, et al., *Scientifica*, 2012:1-15 (2012)).

Several studies have shown that inoculation of commercial crops, such as maize, strawberry and wheat by PGPBs under salt stress results in a decrease of $Na^+$ and an increase of $K^+$ in their shoots and leaves (Nadeem, et al., *Microbiology*, 25:78-84 (2006); Karlidag, et al., *Hortic Sci*, 48:563-567 (2013); Singh and Jha, *Acta Physiol Plant*, 38:110 (2016)). The inoculation of *A. thaliana* and *Trifolium repens*

(white clover) by *Bacillus subtilis* GB03 induced a decrease in the Na$^+$ content in shoots in both species accompanied by an increase or no change in the K$^+$ content (Zhang, et al., *Mol Plant-Microbe Interact*, 21:737-744 (2008); Han, et al., *Front Plant Sci*, 5:525 (2014)).

As used herein, "*Arabidopsis*" refers to the small flowering plant *Arabidopsis thaliana*. *Arabidopsis* is used as a model system for studying plant sciences, including genetics and plant development.

As used herein, "2-keto-4-methylthiobutyric acid (KMBA)" is an intermediate in the methionine salvage pathway. Oxidation of KMBA in certain bacteria leads to the production of ethylene. KMBA can be spontaneously converted to ethylene by photo-oxidation or through the action of plant peroxidases (Chague, et al., *FEMS Microbiol Ecol*, 40:143-149 (2002)), which are abundantly present in the plant apoplast (Minibayeva, et al., *Phytochemistry*, 112:122-129 (2015); Karkonen, et al., *Phytochemistry*, 112:22-32 (2014)).

The term "plant substrate" refers to a substrate commonly used for growing plants, including plant seeds, plant roots and plant seedlings. Non-limiting examples of such plant substrates include, but are not limited to soil, peat, compost, vermiculite, perlite, sand, clay, and combinations thereof.

As used herein, "sodic soil" refers to soil with a disproportionally high sodium content relative to other salts. Sodic soils are characterized by poor soil structure and low infiltration rate. Additionally, they are poorly aerated and difficult to cultivate.

II. Methods for Increasing Plant Tolerance to Abiotic Stresses

Methods and compositions for increasing tolerance to abiotic stresses in plants are provided. The methods include providing the plant with 2-keto-4-methylthiobutyric acid (KMBA) exogenously ("exogenous KMBA method), alone or in combination with modifying the plant with a microbial system that results in production of KMBA in the plant ("endogenous KMBA method"). The exogenous KMBA method include treating seeds, seedlings or mature plants with 2-keto-4-methylthiobutyric acid (KMBA).

One embodiment provides a method for increasing salt tolerance in a plant by treating the plant with an amount of 2-keto-4-methylthiobutyric acid (KMBA) effective to increase salt tolerance in the plant relative to an untreated plant (exogenous KMBA).

The endgenous KMBA method providing seeds, seedlings or mature plants with a microbial system that results in production of KMBA in mature plants. In some embodiments, seeds or plant roots can be inoculated with or coated with a microbial system that results in production of KMBA in mature plants. A preferred microbial system *Enterobacter* sp. SA187. In other embodiments, seeds, seedling and plants can be grown using substrates containing an effective amount of *Enterobacter* sp. SA187 to inhibit or reduce abiotic stress in the plant. Suitable plant substrates include, but are not limited to soil, peat, compost, vermiculite, perlite, sand, clay and combinations thereof. Some embodiments provides a bacterium genetically engineered to express KMBA or increased levels of KMBA relative to an unmodified bacterium, which can be used as a microbial system that results in production of KMBA in mature plants. In a preferred embodiment the bacterium is an endophytic bacterium. The engineered bacterium can be used to inoculate plants and increase tolerance in the plant to abiotic stress conditions.

In another embodiment, *Enterobacter* sp. SA187 produces 2-keto-4-methylthiobutyric acid (KMBA) in the plant (endogenous KMBA) to promote plant tolerance to salt stress.

Still another embodiment includes a combination of endogenous and exogenous KMBA treatment.

In some embodiments, the methods include providing the plant with one or more additional plant-growth promoting bacteria and/or one or more plant growth-promoting rhizobacteria.

A. Exogenous 2-Keto-4-methylthiobutyric Acid (KMBA) Method

Methods for increasing salt tolerance in a plant by treating the plant with an amount of KMBA effective to increase salt tolerance in the plant are provided. In one embodiment, KMBA can be delivered to mature plants. In other embodiments, KMBA can be used to irrigate seeds or seedlings. The plant can be treated with KMBA or KMBA in a solution.

In some embodiments, the amount of KMBA used to treat a plant is at a concentration of 1.0 to 250 nM. The concentration of KMBA can be 1, 5, 10, 20, 30, 40, 50, 60, 70, 80, 90, 100, 125, 150, 175, 200, 225, or 250 nM. In a preferred embodiment, KMBA is present at a concentration of at least 100 nM.

One embodiment provides a method for increasing plant tolerance to abiotic stress by treating the plant with a composition containing an effective amount of KMBA. Exemplary abiotic stress conditions include, but are not limited to drought, high heat, high salt, bright light, ultraviolet light, too high and too low temperatures, freezing, heavy metals and hypoxia. In one embodiment, the abiotic stress can be water salinity, soil salinity, or both.

In one embodiment, plants are treated with an amount of KMBA effective to increase salt tolerance in the plant. The KMBA can be delivered to the plant in solution. In one embodiment, KMBA is delivered in an aqueous solution. The aqueous solution can be water, salt water, or seawater.

Some embodiments provide a method of delivering KMBA to plants in a solution. The solution can contain 1-10% salt. In some embodiments the solution contains 1.5%, 2%, 2.5%, 3%, 3.5%, 4%, 4.5%, 5%, 5.5%, 6%, 6.5%, 7%, 7.5%, 8%, 8.5%, 9%, or 9.5% salt. In a preferred embodiment, the solution contains 3.5% salt. The salt can be selected from the group containing salts of sodium, chloride, sulfate, magnesium, calcium, potassium, or combinations thereof.

B. Edogenous 2-Keto-4-methylthiobutyric Acid (KMBA) Method

*Enterobacter* sp. SA187 is a bacterium that was previously isolated from the desert pioneer plant *Indigofera argentea* Burm.f. (Fabaceae) (Lafi, et al., *Genome Announc*, 9-10 (2017); Andrés-Barrao, et al., *Front Microbiol*, 8:1-21 (2017)). SA187 was deposited on Sep. 24, 2019, with American Type Culture Collection (ATCC), P.O. Box 1549, Manassas, Va. 20110 USA, and given Patent Deposit Number PTA-126210. SA187 was found to colonize both surface and inner plant root and shoot tissues and to modify several plant phytohormone pathways. *Enterobacter* sp. SA187 was shown to significantly increase the yield of the agronomically important crop alfalfa (*Medicago sativa*) in field trials under both normal and salt stress conditions, demonstrating that SA187 has a high potential to improve agriculture under desert conditions. Gene expression analysis of SA187-containing plants indicated an upregulation of the methionine salvage pathway upon plant colonization, increasing the production of 2-keto-4-methylthiobutyric acid (KMBA), which is known to be converted into ethylene in planta.

Methods for providing plants with tolerance to abiotic stress conditions are disclosed in WO 2017/125894. The methods include inoculating the seed or plant with an effective amount ($10^6$-$10^8$ bacteria/ml) of SA187 to provide the seed or plant with resistance to the abiotic stress conditions. The inoculation of the plant can be in the rhizosphere of the plant. The rhizosphere is the area around a plant root that is inhabited by a unique population of microorganisms. Alternatively, the plant root can be inoculated directly. In certain embodiments, the plant root is coated with SA187. The SA187 is preferably the bacterium whose genome contains SEQ ID NO:1, 2, 3, 4, 5, 6, 7, 8, 9, 10, 11, 12, 13, or a combination thereof. More preferably, the SA187 genome contains all of SEQ ID NO:1-13.

Another embodiment use a seed coating composition containing SA187. The SA187 can be encapsulated with a non-toxic, biodegradable coating. The seed coating composition can also contain a coating adhesive. Exemplary seed coating compositions contain gelatin, cellulose, alginate, xanthum, or a combination thereof. Certain seed coating compositions can have multiple layers.

Other embodiment provides a method of improving growth of a seed or plant under abiotic stress conditions by growing the seed or plant in a plant substrate, wherein the plant substrate includes an effective amount of SA187 to colonize the seed or a root of the plant to provide abiotic stress resistance to the seed or plant.

One embodiment provides a plant substrate containing an effective amount of a species of the genus *Enterobacter* to inhibit or reduce abiotic stress in the plant. In a preferred embodiment, the *Enterobacter* species is SA187. Suitable plant substrates include, but are not limited to soil, peat, compost, vermiculite, perlite, sand, clay and combinations thereof. Typically, the plant substrates contain $10^6$ to $10^9$ bacteria per/g of substrate.

The disclosed methods can use bacteria genetically engineered to express KMBA or increased levels of KMBA relative to an unmodified bacterium, which can be used as a microbial system that results in production of KMBA in mature plants. Bacteria can be genetically engineered to overexpress KMBA or increased levels of KMBA relative to an unmodified bacterium using methods known in the art. The data in this application shows that the expression level of most of the genes encoding proteins involved in the methionine salvage pathway were upregulated in SA187 upon plant colonization compared with bacteria incubated for 4 h in liquid ½ MS with or without 100 mM NaCl in the absence of plants. Thus, the disclosed methods include engineering bacteria to overexpress one or more genes involved in the methionine salvage pathway.

Many organisms including bacteria utilize the methionine salvage (FIG. 7F) pathway recycling methylthioadenosine (MTA) to methionine. In a first step in *E. coli*, MTA is hydrolysed by a nucleosidase (EC 3.2.2.16, coded by gene pfs, now mtnN, for methylthioadenosine nucleosidase). Additional genes include: tyrB encoding a wide spectrum aminotransferase the gene encoding MtnA (methylthioribose-1-phosphate isomerase), mtnA, mtnB, which codes for a methylthioribulose-1-phosphate dehydratase; an enolase-phosphatase, encoded by gene mtnC; mtnD (ykrZ), which codes for the aci-reductone dioxygenase (Sekowska, et al., *BMC Microbiology* 2004, 4:9; mtnK was identified encoding methylthioribose kinase (Sekowska, et al., *BMC Microbiology* 2001, 1:15); metK, encoding S-adenosylmethionine (SAM) synthetase; speE encoding spermidine synthetase; speD, encoding S-adenosylmethionine decarboxylase (Gao, et al., MBio, 5(2)e0079-14, (2014); Sekowska, et at, *J. Mol. Microbiol. Biotechnol.* (2000) 2(2); 145-177)). Additionally, the bacteria can be engineered to express L-amino acid deaminase (L-AAD) from *Proteus vulgaris* as disclosed for example in Hossain, et al., *PLOS One,* 9(12):e114291 (2014), for one-step biosynthesis of α-keto-γ-methylthio butyric acid from *E. coli* from L-methionine. Preferred bacteria include SA187 and *E. coli*. However, a suitable bacterium can be selected from the list of bacteria suitable for co-inoculation, described below.

Seed Coating Compositions

One embodiment provides a seed coating composition having at least one layer coating all or part of the seed, wherein at least one layer contains an effective amount of KMBA and/or SA187 to provide the seed or the plant that grows from the seed with resistance to abiotic stress conditions. The SA187 can be from $10^6$/ml to $10^9$/ml of seed coating composition.

Another embodiment provides a seed coating composition containing KMBA. The KMBA can be encapsulated with a non-toxic, biodegradable coating. The seed coating composition can also contain a coating adhesive. Exemplary seed coating compositions contain gelatin, cellulose, alginate, xanthum, or a combination thereof. Certain seed coating compositions can have multiple layers.

In another embodiment, the seed coating composition contains multiple layers for example, 2, 3, 4 or 5 or more layers. KMBA, SA187 and/or one or more additional plant growth promoting bacteria can be in any or all of the layers of the seed coating composition; however, at least one of the layers of a multiple layer seed coating composition contains an effective amount of KMBA and/or SA187 to provide the seed or the plant growing from the seed with resistance to abiotic stress conditions. Preferably, the KMBA and/or SA187 or other plant growth promoting bacteria are in the layer adjacent to the surface of the seed.

In one embodiment, at least one layer contains guar gum, derivative guar, polyacrylamide, poly(methacrylic acid), poly(acrylic acid), polyacrylate, poly(ethylene glycol), phosphonate-end capped polymers, polyethyleneoxide, poly (vinyl alcohol), polyglycerol, polytetrahydrofuran, polyamide, hydroxypropyl guar, carboxymethyl guar, carboxymethyl hydroxypropyl guar, starch, derivatized (e.g., cationic) starch, corn starch, wheat starch, rice starch, potato starch, tapioca, waxy maize, sorghum, waxy sorghum, sago, dextrin, chitin, chitosan, alginate compositions, xanthan gum, carageenan gum, gum karaya, gum arabic, pectin, cellulose, hydroxycellulose, hydroxyalkyl cellulose, hydroxyethyl cellulose, carboxymethylhydroxyethyl cellulose, hydroxypropyl cellulose, a derivative of any of the foregoing or a combination of any of the foregoing. As non-limiting examples, the layer can contain a 90 wt % derivatized guar and 10 wt % starch (or derivatized starch) mixture, or a 60 wt % hydroxypropyl guar and 40 wt % carboxymethyl hydroxypropyl guar mixture.

In some embodiments, the layer can act as a carrier coating. Fungicides and beneficial microbes that protect the seed and emerging seedling are carried in the carrier coating. For example, alfalfa seed coating with incorporated KMBA and/or SA187 is used to inoculate the field in which desired crop plants are planted or are growing.

Another embodiment provides agglomerates of seed. The agglomerate or grouping of seed is a grouping of 2 or more individual seeds together. The seeds can be for the same plant or for different plants. In another embodiment, the agglomerate is a grouping of more than 5 individual seeds together. In a further embodiment, the agglomerate is a grouping of more than 10 individual seeds together. In yet another embodiment, the agglomerate is a grouping of more than 25 individual seeds together. In yet a further embodiment, the agglomerate is a grouping of more than 50 individual seeds together. In another embodiment, the agglomerate is a grouping of more than 100 individual seeds together.

1. Seed Agglomerates

The agglomeration of seed can aid in the application of the seed coating composition because the seed coating composition, when using an agglomeration of seed, can be shaped or formed to be consistent in shape or form. For example, the agglomeration can be formed as spherical or substantially spherical, thus allowing the seed coating composition to be likewise substantially spherical. This can allow for improved or more consistent casting or spraying, can minimize the occurrence of blockage or clogging of the nozzles, hoses, etc. due to uneven particle size distribution. Typically, a binder or adhesive is utilized to bunch (e.g., agglomerize) the grouping of seeds together.

The agglomeration can also aid in seed or seedling establishment as a layer of the wetting agent (or other layer than affects the soil) can be concentrated to a local area of soil, thus, increasing its chance of wetting the soil surrounding the seed(s). the agglomeration can also promote survival by allowing the seeds, when germinating into seedlings, to generate sufficient force to penetrate hydrophobic areas or soil such as, for example, a hydrophobic (i.e., encrusted) soil surface In one embodiment, the seed coating composition contains an agglomeration of seeds of from between 2 seeds to 100 seeds, typically between 2 to 50 seeds, typically between 2 to 25 seeds; and at least one layer selected from the group consisting a layer of a filler, a layer of a binding agent, a layer of a wetting agent, a layer of an anti-bacteria agent, a layer of an active ingredient and any combination thereof.

In one embodiment, the seed coating composition is of substantially uniform size of from between 10 micrometers and 4 mm in diameter. In another embodiment, the seed coating composition is of substantially uniform size of from between 25 micrometers and 2 mm in diameter. In a further, the seed coating composition is of substantially uniform size of from between 500 micrometers and 2 mm in diameter.

2. Binder

The seed coating composition can also contain a binder as one of the layers, the binder is sometimes referred to as an adhesive. In one embodiment, the binder can include but is not limited to molasses, granulated sugar, alginates, karaya gum, guar gum, tragacanth gum, polysaccharide gum, mucilage or any combination of the foregoing. In another embodiment, the binder is chosen from, but is not limited to, gelatin, polyvinyl acetates, polyvinyl acetate copolymers, polyvinyl alcohols, polyvinyl alcohol copolymers, celluloses (including ethylcelluloses and methylcelluloses, hydroxypropylcelluloses, hydroxymethyl celluloses, hydroxymethylpropyl-celluloses), polyvinylpyrolidones, dextrins, malto-dextrins, polysaccharides, fats, oils, proteins, gum arabics, shellacs, vinylidene chloride, vinylidene chloride copolymers, calcium lignosulfonates, acrylic copolymers, starches, polyvinylacrylates, zeins, carboxymethylcellulose, chitosan, polyethylene oxide, acrylimide polymers and copolymers, polyhydroxyethyl acrylate, methylacrylimide monomers, alginate, ethylcellulose, polychloroprene, syrups or any combination of the foregoing.

3. Active Ingredients

The seed coating compositions can also include one or more active ingredients in one or more of the layers of the coating. Compounds suitable as active ingredients, which in some embodiments form all or part of at least one layer of the seed coating composition, include but are not limited to herbicides, plant growth regulators, crop desiccants, fungicides, insecticides, insect repellants, and combinations thereof. Suitable pesticides include, for example, triazine herbicides; sulfonylurea herbicides; uracils; urea herbicides; acetanilide herbicides; and organophosphonate herbicides such as glyphosate salts and esters. Suitable fungicides include, for example, nitrilo oxime fungicides; imidazole fungicides; triazole fungicides; sulfenamide fungicides; dithio-carbamate fungicides; chloronated aromatic; and dichloro aniline fungicides. Suitable insecticides, include, for example, carbamate insecticides; organo thiophosphate insecticides; and perchlorinated organic insecticides such as methoxychlor. Suitable miticides include, for example, propynyl sulfite; triazapentadiene miticides; chlorinated aromatic miticides such as tetradifan; and dinitrophenol miticides such as binapacryl. Other active ingredients can include adjuvants, surfactants, and fertilizers.

4. Filler

The seed coating composition can also include at least one filler as all or part of a layer. In one embodiment, the filler is selected from the group consisting of wood flours, clays, activated carbon, carbohydrates, sugars, dextrins, maltodextrins, diatomaceous earth, cereal flours, wheat flour, oat flour, barley flour, fine-grain inorganic solids, calcium carbonate, calcium bentonite, kaolin, china clay, talc, perlite, mica, vermiculite, silicas, quartz powder, montmorillonite or mixtures thereof.

5. Nutrients

The seed coating composition can also contain a nutrient such as a micronutrient or macronutrient in one or more layers of the seed coating composition. The nutrient can be in all or part of a layer. The nutrient can also be included with the grouping of seeds as part of the binder or adhesive. "Nutrient" as used herein can refer to an additive or substance utilized by plants, grasses, shrubs for plant, grass, and shrub growth, respectively. Macronutrients can be utilized in larger amounts by plants, grasses, etc. in proportionally larger amounts relative to micronutrients. Nutrients include but are not limited to manganese, boron, copper, iron, chlorine, molybdenum, and zinc, potassium, nitrogen, calcium, magnesium phosphorus and sulfur, among others. The seed coating compositions can include various combinations and relative amounts of individual macronutrients.

Co-inoculation

Plants and seeds can be co-inoculated with SA187 and one or more other plant growth-promoting bacteria or rhizobacteria to provide the seeds or plants with resistance or tolerance to abiotic stress conditions. Co-inoculation is based on mixed inoculants, combination of microorganisms that interact synergistically, or when microorganisms such as *Azospirillum* are functioning as "helper" bacteria to enhance the performance of other beneficial microorganisms. In the rhizosphere the synergism between various bacterial genera such as *Bacillus, Pseudomonas* and *Rhizobium* has been demonstrated to promote plant growth and development. Compared to single inoculation, co-inoculation can improve the absorption of nitrogen, phosphorus and mineral nutrients by plants.

Suitable bacteria that can be co-inoculated with SA187 include but are not limited to *Pseudomonas putida, Pseudomonas aeruginosa, Klebsiella* sp., *Enterobacter asburiae, Rhizobium* sp. (pea), *Mesorhizobium* sp., *Acinetobacter* spp., *Rhizobium* sp.(lentil), *Pseudomonas* sp. A3R3, *Psychrobacter* sp. SRS8, *Bradyrhizobium* sp.,

*Pseudomonas aeruginosa* 4EA, *Pseudomonas* sp., *Ochrobactrum cytisi*, *Bacillus* species PSB10, *Paenibacillus polymyxa*, *Rhizobium phaseoli*, *Rahnella aquatilis*, *Pseudomonas fluorescens*, *Ralstonia metallidurans*, *Azospirillum amazonense*, *Serratia marcescens*, *Enterobacter* sp., *Burkholderia*, *Pseudomonas jessenii*, *Azotobacter* sp., *Mesorhizobium ciceri*, *Azotobacter chroococcum*, *Klebsiella oxytoca*, *Pseudomonas chlororaphis*, *Baciilus subtilis*, *Gluconacetobacter, diazotrophicus*, *Brevibacillus* spp., *Bravibacterium* sp., *Xanthomonas* sp. RJ3, *Azomonas* sp. RJ4, *Pseudomonas* sp. RJ10, *Bacillus* sp. RJ31, *Bradyrhizobium japonicum*, *Variovorax paradoxus*, *Rhodococcus* sp., *Flavobacterium*, *Sphingomonas* sp, *Mycobacterium* sp, *Rhodococcus* sp, *Cellulomonas* sp., *Azospirillum* sp., *Azospirillum brasilense*, *Rhizobium meliloti*, *Kluyvera ascorbata*, *Rhizobium cicero*, *Rhizobium leguminosarum*, *Paenibacillus polymyxa* strain A26, a *Alcaligenes faecalis* strain AF, and combinations thereof.

In some embodiments, the inoculation method does not include inoculating the plant or seeds with SA187. In these embodiments, the exogenous KMBA method is employed in seeds/plants inoculated one or more other plant growth-promoting bacteria or rhizobacteria to provide the seeds or plants with resistance or tolerance to abiotic stress conditions C. Coating Techniques Equipment utilized to for coating seeds with the disclosed seed coating compositions include, but are not limited to drum coaters, rotary coaters, tumbling drums, fluidized beds and spouted beds to name a few. The seeds can be coated via a batch or continuous coating process.

The seeds can be separated prior to coating which, in one embodiment, utilizes mechanical means such as a sieve. The separated seeds can then be introduced into a coating machine having a seed reservoir. In one embodiment, the seeds in the mixing bowl are combined with one or more of the coatings described herein and adhered with a binder or adhesive.

In one embodiment of the process, one or more layers as described herein can be added to coat the seed or agglomeration. Outer layers can be introduced sequentially to the rotating drum.

In another embodiment, agglomerators or agglomerator devices may also be utilized. Coating is performed within a rotary coater by placing seeds within a rotating chamber, which pushes the seeds against the inside wall of the chamber. Centrifugal forces and mixing bars placed inside the coater allow the seed to rotate and mix with a coating layer. Binder or other coating materials can be pumped into the proximate center of the coater onto an atomizer disk that rotates along with the coating chamber. Upon hitting the atomizer disk, liquid adhesive is then directed outward in small drops onto the seed.

In one embodiment, seed coating techniques include, for example, seed in a rotating pan or drum. Seed is then misted with water or other liquid and then gradually a fine inert powder, e.g., Diatomaceous earth, is added to the coating pan. Each misted seed becomes the center of a mass of powder, layers, or coatings that gradually increases in size. The mass is then rounded and smoothed by the tumbling action in the pan, similar to pebbles on the beach. The coating layers are compacted by compression from the weight of material in the pan. Binders often are incorporated near the end of the coating process to harden the outer layer of the mass. Binders can also reduce the amount of dust produced by the finished product in handling, shipping and sowing. Screening techniques, such as frequent hand screening, are often times utilized to eliminate blanks or doubles, and to ensure uniform size. For example, tolerance for seed coating compositions described herein can be about 1/64th inch (0.4 mm), which is the US seed trade standard for sizing.

In yet another embodiment, the seed coating compositions and methods described herein comprises "in situ coating". In situ coating means, in one embodiment, where a raw or non-coated seed is implanted in a hole, cavity or hollowed area in the ground and immediately or soon thereafter a coating composition is sprayed or applied directly into the hole, cavity or hollowed area to surround or partially surround the seed. Typically, the application of the seed as well as application of the coating composition are performed mechanically, but is understood that either or both of the referenced applications can be performed manually as well.

The coating can also be applied to a seed by spraying, dipping or brushing.

D. Cultivation Methods

One embodiment provides a method of cultivating a plant by planting seeds or seedlings of the plant and irrigating the seeds or seedlings with a saline solution containing KMBA. The plant can be a forage crop. In one embodiment the forage crop is selected from the group containing rice, wheat, sugarcane, maize, soybean, cotton, vegetables, rape, mustard, sorghum, millet, grass, *Brassica* spp., rapeseed, barley, hay, and alfalfa.

Another embodiment provides a method of cultivating plants in sodic soil by contacting the plant in the sodic soil with an effective amount of KMBA to increase salt tolerance in the plant.

In embodiments combining the exogenous and endogenous KMBA methods, seeds or plants inoculated with an effective amount of SA187 to provide the seed or plant with resistance or tolerance to abiotic stress condition are cultivated in sodic soil by contacting the plant in the sodic soil with an effective amount of KMBA to increase salt tolerance in the plant. Preferred seeds and plants, preferably roots that can be inoculated with or coated with SA187 include, but are not limited to alfalfa, cotton, wheat, maize, soybean, oat, barley, potato, and sugar beets.

E. Irrigation Solution

An irrigation solution to increase salt tolerance in plants is provided. The irrigation solution contains 1.0 to 250 nM KMBA in an aqueous saline solution. In one embodiment the solution contains 1, 5, 10, 20, 30, 40, 50, 60, 70, 80, 90, 100, 125, 150, 175, 200, 225, or 250 nM of KMBA. In a preferred embodiment, KMBA is present at a concentration of at least 100 nM.

In one embodiment the aqueous saline solution is seawater. The aqueous solution can contain 1% to 10% salt. In some embodiments the solution contains 1.5%, 2%, 2.5%, 3%, 3.5%, 4%, 4.5%, 5%, 5.5%, 6%, 6.5%, 7%, 7.5%, 8%, 8.5%, 9%, or 9.5% salt. In a preferred embodiment, the solution contains 3.5% salt.

EXAMPLES

Data Submission

RNAseq data are available under the ID GSE102950 which is incorporated by reference in its entirety.

The isolation of SA0187 is previously disclosed in WO 2017/125894. Briefely, *Enterobacter* sp. SA187 (endophytic bacteria) was isolated from surface sterilized root nodules formed on roots of pioneer plant *Indigofera argentea* Burm.f. (Fabaceae). Plants were collected from different regions in the Jizan area (16° 56.475' N, 42° 36.694' E) of Saudi Arabia. SA187 has been shown to possess plant growth promoting activities, such as the production of siderophores and indole acetic acid (IAA).

Sequencing

The genomic DNA of SA187 was extracted using the Qiagen's DNeasy blood and tissue kit following the manufacturer protocol. The DNA was then sequenced using paired-end Illumina MiSeq and the library preparation was constructed as described previously (1). Contig assembly was done with Spades assembler version 3.6 (4) with a 1 KB contig 52 cutoff size.

Total RNA was extracted from 5-day-old plants inoculated or not with SA187 and transferred for 10 more days on ½ MS plates with or without 100 mM NaCl using the Nucleospin RNA plant kit (Macherey-Nagel), including DNase treatment, and following manufacturer's recommendations.

RNA samples were used for Illumina HiSeq deep sequencing (Illumina HiSeq 2000, Illumina). Three biological replicates were processed for each sample. Paired-end sequencing of RNA-seq samples was performed using Illumina GAIIx with a read length of 100 bp. Reads were quality-controlled using FASTQC (http://www.bioinformatics.babraham.ac.uk/projects/fastqc/). Trimmomatic was used for quality trimming[8]. Parameters for read quality filtering were set as follows: Minimum length of 36 bp; Mean Phred quality score greater than 30; Leading and trailing bases removal with base quality below 3; Sliding window of 4:15. TopHat v2.0.9[9] was utilized for alignment of short reads to the *Arabidopsis thaliana* genome TAIR10 (Supplementary Table 1), Cufflinks v2.2.0[10] for transcript assembly and differential expression. To identify differentially expressed genes, specific parameters (p-value: 0.05; statistical correction: Benjamini Hochberg; FDR: 0.05) in cuffdiff were used. Post-processing and visualization of differential expression were done using cummeRbund v2.0.0[11]. Gene is considered as regulated if fold change $>\log2^{10.61}$ and q-value $<0.05$. Results were confirmed by analyzing 12 genes using qPCR method.

For qPCR analysis, plant RNAs were purified as described previously. For bacterium, SA187 incubated 4 h in ½ MS or ½ MS+100 mM, at 28° C., under the dark, were used for RNA extraction, using the RiboPure™ RNA Purification Kit, bacteria (Ambion) following manual instructions for Gram-(-) bacteria, with the exception that no beads were used during bacterial lysis. RNA extraction was followed by DNAseI treatment in order to obtain purified total RNA.

cDNAs were synthetized using SuperscriptIII (Invitrogen), 1 μg of total RNA and oligo-dT following manufacturer's recommendations. For *Arabidopsis* gene expression analyses, ACTIN2 (At3g18780) and UBIQUITIN 10 (At4g05320) were used as reference genes. For SA187 gene expression analyses, infB, rpoB and gyrB were used as reference genes. All reactions were done in a CFX96 Touch™ Real-Time PCR Detection System (BIO-RAD) as follows: 50° C. for 2 min, 95° C. for 10 min; 40×[95° C. for 10 sec and 60° C. for 40 sec]; and a dissociation step to validate the PCR products. All reactions were performed in three biological replicates, and each reaction as a technical triplicate. Gene expression levels were calculated using Bio-Rad CFX manager software.

Hierarchical Clustering and Gene Family Enrichment

*Arabidopsis* regulated genes were used to generate HCL tree using Multi Experiment Viewer (McV 4.9.0 version, TM4, https://sourceforge.net/projects/mev-tm4/files/mev-tm4/MeV%204.9.0/). Raw data were normalized for every gene and transformed in log2. Hierarchical clustering was performed using Euclidian distances, average linkage and leaf order optimization. Heat colors indicate log2 fold change. Gene enrichment analyses were performed using AmiGO website (http://amigo1.geneontology.org/cgi-bin/amigo/term_enrichment). Each cluster were analyzed using default parameter.

Results

De novo assembly of MiSeq reads for *Enterobacter* sp. SA187 resulted in 14 contigs with a total length of 4,404,403 bp and a mean contig size of 314,600 bp. The N50 was 2,296,004 bp and the L50 has been reached in 1 contig. The GC content of this draft genome was 56%. Megablast comparison of the SA187 concatenated contigs against the NCBI reference genome database (http://www.ncbi.nlm.nih.gov/genome/) revealed the 57 closest relative genomes being *Enterobacter sacchari* SP1 with a coverage of 63% and sequence identity of 95% (Accession number NZ_CP007215.2). The annotation of *Enterobacter* sp. SA187 was carried out using the default INDIGO pipeline (7) with the exception of open reading frame (ORFs) prediction by FragGeneScan. The annotation of SA187 resulted in 3,087 ORFs, 9 rRNA, 75 tRNA, and 145 ncRNA.

The annotation predicted a number of siderophore pathway genes such as entE, entC, entA, entB, entF, as well as entS, an MFS transporter of enterobactin. An ABC transporter involved in iron uptake, sitABCD, was also found, as well as five copies of the iron complex outer membrane receptor (fhuA) and a TonB-dependent outer membrane iron-enterobactin/colicin (fepA). Generally, PGPR bacteria enhance plant growth through the synthesis of IAA from tryptophan via indole pyruvate as the main pathway (9). The SA187 genome harbors a number of genes involved in this pathway, but lacks the gene encoding for indolepyruvate decarboxylase (ipdC). Moreover, the SA187 genome codes for the enzyme tryptophanase (TnaA) (EC: 4.1.99.1), which can transform tryptophane into indole.

Genome of *Enterobacter* sp. SA187 has been deposited at DBJ/EMBL/GenBank under accession number MORB00000000 (which is incorporated herein in its entirety. The genome of SA187 contains SEQ ID NO:1-13.

Results

Based on 16S rDNA sequencing and comparison, SA187 was suggested to belong to the *Enterobacter* genus, with high homology with *Enterobacter kobei* strains.

The 16S ribosomal RNA gene sequence (or 16S rRNA) is deposited at DDBJ/EMBL/GenBank under the accession no KY194757.

Based on the 16S rRNA gene sequence the SA187 is closely related to *Enterobacter kobei* CCUG 49023$^T$ and *Enterobacter aerogenes* strain KCTC 2190 with 99% sequence similarity. SA187 comprises SEQ ID NO:1, 2, 3, 4, 5, 6, 7, 8, 9, 10, 11, 12, 13, or a combination thereof.

Example 1: *Enterobacter* sp. SA187 Increases Alfalfa Yield in Field Trials Under Field Conditions Methods Field Trials To inoculate alfalfa seeds (*Medicago sativa* var. CUF 101), a slurry was prepared consisting of sterilized peat, a broth culture of SA187, and sterilized sugar solution (10%) in the ratio 5:4:1 (w/v/v). Subsequently, alfalfa seeds were coated with the slurry at a rate of 50 mL·kg$^{-1}$. As a control, seeds were coated with a similar mixture without bacteria. Field trials were conducted at the experimental station in Hada Al-Sham (N 21°47'47.1" E 39°43'48.8"), Saudi Arabia, in winter seasons 2015-2016 and 2016-2017. The experiment was a randomized complete block design with a split-split plot arrangement of four replicates in the season 2015-2016 season and three replicates in the 2016-2017 season, plots (2×1.5 m) with seed spacing 20 cm row-to-row. The field was irrigated using ground water with two different salinity levels: low salinity (EC =3.12 dS·m$^{-1}$), and high salinity (EC=7.81 dS·m$^{-1}$). The soil had an average pH 7.74 and salinity EC=1.95 dS·m$^{-1}$. Agronomical data (plant height, fresh biomass, and dry biomass) were recorded every 25-30 days from each harvest; three harvests were done in the first season, four harvests in the second season.

Results

Figure 1D:
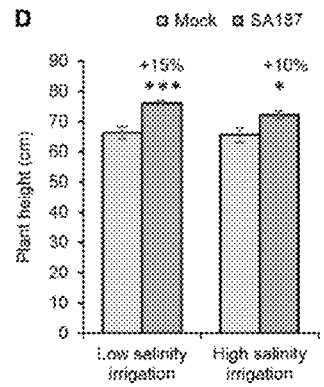
Figure 1E:
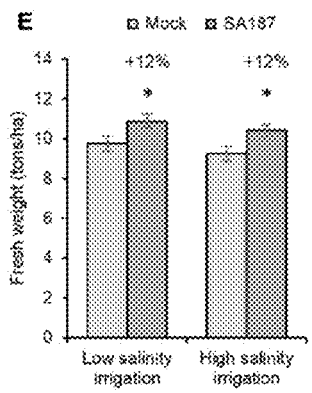
Figure 1F:
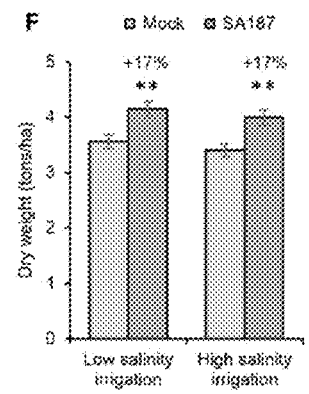

Since SA187 was an outstandingly performing bacterial isolate in a previous screen using *Arabidopsis* as a model plant (Andrés-Barrao, et al., *Front Microbiol*, 8:1-21 (2017)), the potential agronomic use of SA187 as a biological solution for agriculture was evaluated. Therefore, the beneficial activity of SA187 on different growth parameters of the crop plant alfalfa (*Medicago sativa*), which is largely used as animal feed in different regions of the world, was tested. Alfalfa seeds were coated with SA187 and tested in parallel with mock-coated seeds in the experimental fields' station near the city of Jeddah, Saudi Arabia. A randomized complete block design with a split-split plot arrangement with different replicates was used over two subsequent growth seasons (2015-2016 and 2016-2017). In the first growing season, using low saline water (EC=3.12 dS·m$^{-1}$) irrigation, SA187-inoculated alfalfa plants exhibited an increase of 25% for plant height, leading to an increase of both fresh and dry biomass by 16% and 14%, respectively (FIG. 1A, B, C). Interestingly, using high saline irrigation water (EC=7.81 dS·m$^{-1}$), a similar impact on the plant growth was observed. In the growing season 2016-2017, although there was no clear difference in the alfalfa yield between plots irrigated with low and high saline water, a beneficial impact of SA187 was still observed on both experimental plots irrigated with low and high saline water (FIG. 1D, E, F). The lowered increase in growth parameters in the second season is most likely due to exceptional rainfalls in that period. In conclusion, SA187 can efficiently improve crop productivity under extreme agricultural conditions.

Example 2: *Enterobacter* sp. SA187 Enhances Salt Tolerance in *Arabidopsis thaliana*

Methods

Endophytic Bacteria, Plant Material, Growth Condition and Physiological Experiments

*Enterobacter* sp. SA187 was previously isolated from root nodules of the leguminous pioneer plant *Indigofera argentea* in the Jizan region of Saudi Arabia (Lafi, et al., *Genome Announc*, 9-10 (2017); Andres-Barrao, et al., *Front Microbiol*, 8:1-21 (2017)). The complete genome sequence of *Enterobacter* sp. SA187 is known in the art (Andres-Barrao, C., et al., *Front Microbiol*. 8:1-21 (2017)). *Arabidopsis* seeds were obtained either from publicly available collections or provided by Dr. Jean Colcombet (IPS2, Orsay, France). The following mutant lines used in this study were published previously: the JA-receptor coi1-1 mutant (Xie, et al., *Science*, 280:1091-1094 (1998)), JA-insensitive jar1-1 (Staswick, et at, *Proc Natl Acad Sci USA*, 89:6837-6840 (1992)), the ABA biosynthesis aba2-1 mutant (Schwartz, et al., *Plant Physiol*, 114:161-166 (2997)), the ABA receptor quadruple pyr1-1pyl1-1pyl2-1pyl4-1 mutant (Park et al., *Science*, 324:1068-1071 (2009)), the ethylene insensitive ein2-1 (Guzmán, et al., *Plant Cell*, 2:513-523 (1990)) and ein3-1 mutants (Roman, et al., *Genetics*. 139:1391-1409 (1995)), the heptuple ethylene-biosynthesis deficient mutant acs1-1acs2-1acs4-1acs5-2acs6-1acs7-1acs9-1 (Tsuchisaka, et al., *Genetics*, 183:979-1003 (2009)), and the ethylene-dependent pEBF2::GUS reporter (Konishi and Yanagisawa, *Plant J*, 55:821-831 (2008)).

Prior to every experiment, *A. thaliana* seeds were surface sterilized 10 min in 70% ethanol+0.05% sodium dodecyl sulfate on a shaker, washed 2 times in 96% ethanol and let to dry. To ensure SA187-inoculation, sterilized seeds were sown on ½ MS plates (Murashige and Skoog basal salts, Sigma) containing SA187 (2·10$^5$ cfu·ml$^{-1}$), stratified for 2 days at 4° C. in the dark and then placed vertically to growth conditions for 5 days. The ½ MS plates with SA187 were prepared by addition of a calculated amount of bacterial suspension to pre-cooled agar medium during plate preparation.

Average length of root hairs was determined based on images of 5-day-old roots (1 image per root at constant distance from the root tip, 25 seedlings per condition) or 16-day-old roots (along the whole primary root length grown after transfer) captured by a Nikon AZ100M microscope equipped with an AZ Plan Apo 2× objective and a DS-Ril camera (Nikon). All root hairs in focus were measured using ImageJ. Average values and standard deviations were calculated from 10% longest root hairs to eliminate non-developed root hairs and describe the maximal elongation capacity of root hairs.

For salt stress tolerance assays, 5-day-old seedlings were transferred onto ½ MS plates with or without 100 mM NaCl (Sigma). Primary root length was measured every 2 days using ImageJ software after scanning the plates. Lateral root density was evaluated as detectable number of lateral roots under a stereo microscope divided by the primary root length. Fresh weight of shoots and roots was measured 12 days after transfer of seedlings. Dry weight was measured after drying shoota and roots for 2 days at 70° C. Following Koch's postulate, SA187 was re-isolated from *Arabidopsis* root system at the end of an initial experiment to confirm the genotype of the inoculated strain. To address the ethylene involvement in *Arabidopsis* adaptation to salt stress, ACC (1-aminocyclopropane-1-carboxylic acid, Sigma), KMBA (2-keto-4-methylthiobutyric acid, Sigma), AVG (aminoethoxyvinylglycine, Sigma), AgNO$_3$ (silver nitrate, Sigma) were added into pre-cooled ½ MS agar medium together with 100 mM NaCl. For DNPH (2,4-dinitrophenylhydrazine, Sigma), 5 mM solution was prepared by solubilizing DNPH into 2M HCl as described previously (Primrose, *J Gen Microbiol*, 98:519-528 (1977)), then the solution was diluted until reaching 1 mM, and equilibrated to the same pH as MS medium (pH 5.8) using 2M KOH. DNP was used at final concentration 3 μM.

All plants were grown in long day conditions in growth chambers (Percival; 16 h light/8 h dark, 22° C.). Each experiment was performed at least in three biological replicates.

Results

Figure 2A:
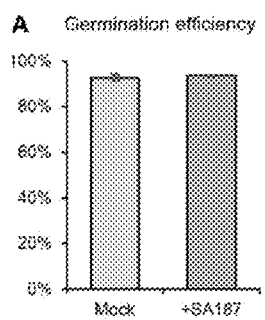
Figure 2B:
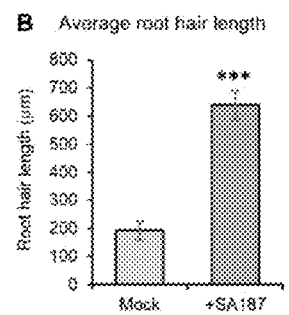
Figure 2C:
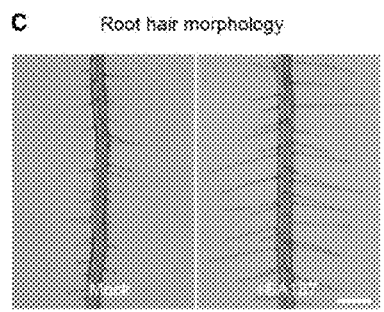
Figure 2D:
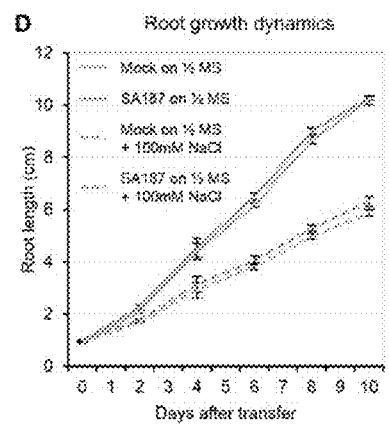

To better understand the molecular mechanism how SA187 confers stress tolerance to plants, model genetic plant *A. thaliana* was used. The capacity of SA187 to affect the early stages of *Arabidopsis* development under normal conditions (½ MS agar medium, 22° C., 16 h of light) was assessed. When compared to mock-inoculated plants, SA187 had no influence on the germination rate of *Arabidopsis* seeds (FIG. 2A), and apart from considerably longer root hairs (FIG. 2B, C), 5-day-old seedlings showed no morphological changes. Similarly, after transfer onto new ½ MS plates, no differences between 17-day-old mock- and SA187-inoculated seedlings were recorded, when measuring root length (FIG. 2D-E), lateral root density (FIG. 2J), shoot morphology (FIG. 2E), or root and shoot fresh and dry weight of seedlings (FIG. 2F-I) indicating that SA187 has no effect on *Arabidopsis* development under normal growth conditions.

On the other hand, the stress tolerance promoting capacity of SA187 on *Arabidopsis* growth was highlighted under salt stress. Five days after germination, SA187- and mock-inoculated seedlings were transferred onto ½ MS agar plates supplemented with 100 mM NaCl, and the same growth parameters were evaluated as above up to 12 days after the transfer to salt plates. SA187-inoculated plants showed stress tolerance promoting activity on salt stress: the shoot and root systems of SA187-inoculated plants were significantly more developed than those of mock-inoculated plants (FIG. 2E-J). While primary root length was similar between SA187- and mock-inoculated plants (FIG. 2D), lateral root density was significantly increased (FIG. 2J). Similarly to 5-day-old seedlings, SA187-inoculated plants at this stage had more than twice longer root hairs compared to the mock-inoculated ones under both normal and salt stress conditions. Moreover, it was proven that the beneficial activity of SA187 was largely linked to living bacterial cells as dead SA187 cells killed by heat-inactivation did not induced any beneficial activity.

Overall, SA187 strongly enhanced *Arabidopsis* growth with increased total fresh and dry weights of both shoot and root under salt stress conditions.

Example 3: *Enterobacter* sp. SA187 Modifies Root and Shoot $K^+$ Levels

Methods $Na^+$ and $K^+$ Content Determination

Dry rosettes and root systems were weighted. All samples were measured individually except for salt-treated root systems, whereby pools of three root systems were measured to ensure proper weight measurements. Sodium and potassium concentrations were prepared for shoot and root dry samples by adding 1 mL of freshly prepared 1% $HNO_3$ (nitric acid, Fisher Scientific) to the pre-weighed samples. The concentrations of sodium and potassium were determined, using Inductively Coupled Plasma Optical Emission Spectrometer (Varian 720-ES ICP OES, Australia).

Results

Figure 3A:
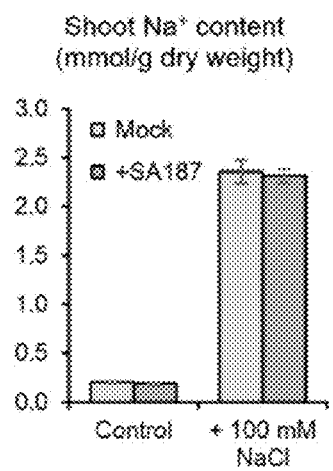
FIGS. 3A-3F show ion content in *Arabidopsis* seedlings.
Figure 3B:
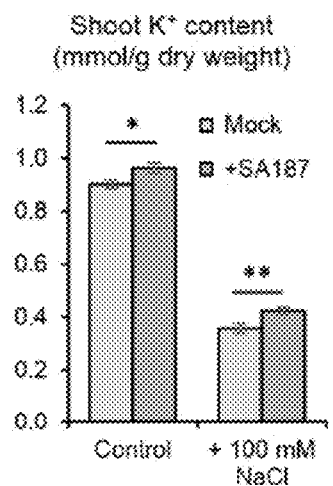
Figure 3C:
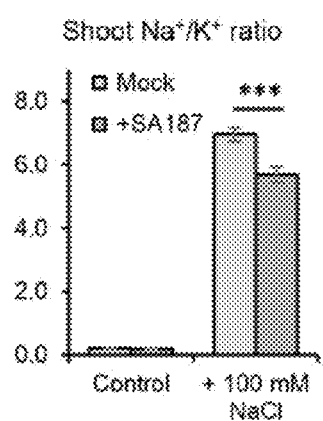
Figure 3D:
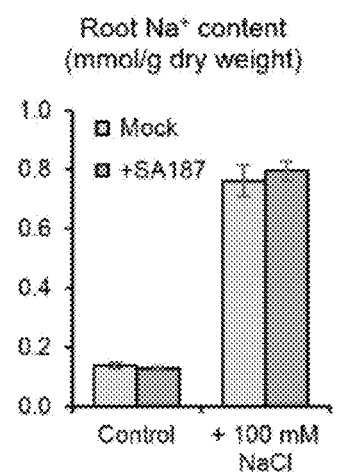
Figure 3E:
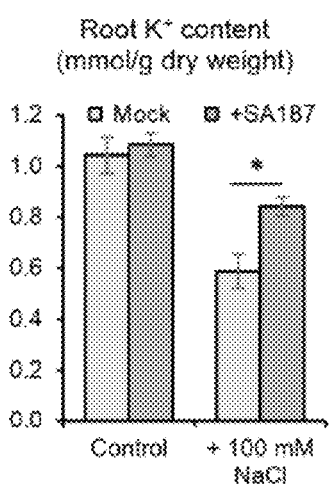
Figure 3F:
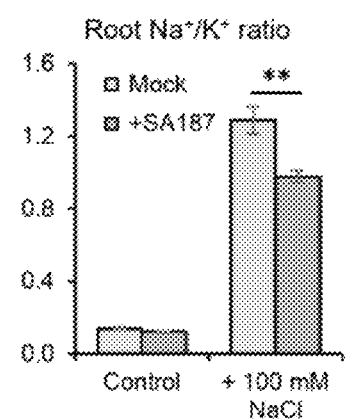

The concentration of sodium ($Na^+$) and potassium ions ($K^+$) in shoots is an important parameter for salt stress tolerance (Garriga, et al., *J Plant Physiol*, 210:9-17 (2017)). Therefore, the $Na^+$ and $K^+$ contents were determined in *Arabidopsis* organs in the absence and presence of SA187. Interestingly, both shoots and roots of SA187-inoculated plants accumulated similar levels of $Na^+$ compared with mock-inoculated plants, under normal and salt stress conditions (FIG. 3A, D). However, increased $K^+$ levels were found in SA187-colonized plants (FIG. 3B, E), resulting in significantly reduced shoot and root $Na^+/K^+$ ratios under saline conditions (FIG. 3C, F), which may help the inoculated plants to keep high growth rate.

Example 4: *Enterobacter* sp. SA187 Colonizes Epidermis and Inner Tissues of Both Roots and Shoots Methods Generation of GFP-Labeled Bacteria SA187 was genetically labeled with the GFP expressing cassette by taking advantage of the mini-Tn7 transposon system (Choi, et al., *Nat Methods*, 2:443-448 (2005)). In order to specifically select for a bacterium carrying the GFP integration in the genome, a spontaneous rifampicin resistant mutant of the strain was obtained first (Crotti, et al., *Environ Microbiol*, 11:3252-3264 (2009)): an overnight-grown culture of SA187 was plated on LB plates supplemented with 100 μg·mL$^{-1}$ of rifampicin, and the plates were incubated for 24 h at 28° C. At least 10 colonies, representing spontaneous rifampicin resistant mutants of the strain were streaked twice on LB plates containing 100 μg·mL$^{-1}$ of rifampicin and thereafter twice on LB plates supplemented with 200 μg·mL$^{-1}$ of rifampicin. The GFP expressing cassette was introduced in the SA187 Rif$^R$ strain by conjugation as described in Lambertsen et al. (*Environ Microbiol*, 6:726-732 (2004)). Briefly, $10^{10}$ cells of SA187 Rif$^R$ strain were mixed with $10^9$ cells of *E. coli* SM10λpir harboring the helper plasmid pUX-BF13, the GFP donor (a mini-Tn7) plasmid and mobilizer pRK600 plasmid. The mixed culture was incubated on sterile nitrocellulose filter for 16 hrs. The conjugation culture of bacterial cells was resuspended in saline buffer (9 g/L NaCl) and spread on selective media with a propitiate antibiotics to select transformed SA187. The selected colonies were screened by fluorescence microscopy for GFP fluorescence and positive colonies were further subjected to genotype confirmation by 16S rRNA gene sequencing.

Confocal Microscopy

GFP-labeled SA187 on *Arabidopsis* roots was imaged using an inverted Zeiss LSM 710 confocal microscope equipped with Plan-Apochromat 10×/0.45, Plan-Apochromat 20×/0.8, and Plan-Apochromat 40×/1.4 Oil objectives. Seedlings grown for 3-21 days on vertical ½ MS agar plates or in soil inoculated with SA187-GFP were washed gently in sterile distilled water and transferred on a sterile agar plate. A block of agar with several seedlings was immediately cut out and placed upside-down to a chambered cover glass (Lab-Tek™ II) with 30 μM propidium iodide (PI) in water as mounting medium. The GFP and PI fluorescence was excited using the 488 nm laser line, and captured as a single track (emission of 493-537 nm for the GFP channel, 579-628 nm for the PI channel, 645-708 nm for chloroplast autofluorescence). For 3D reconstructions, 1 μm-step Z-stacks were taken, and images were generated in the integral 3D view of the Zen software (Zeiss).

Quantification of Root Colonization

Col-0 seedlings were germinated on ½ MS agar plates, and transferred to new ½ MS plates with or without 100 mM NaCl 15 days after germination (10 seedlings per plate). Parts of their root systems grown after the transfer were cut, gently washed by dipping in distilled water to remove non-attached bacterial cells, and then grinded in Eppendorf tubes using teflon sticks. Each sample was resuspended in 1 ml of extraction buffer (10 mM $MgCl_2$, 0.01% Silwet L-77), sonicated for 1 min and subsequently vortexed for 10 min. Samples were diluted in 10× scale, spread on LB Petri dishes, and colonies were counted after overnight incubation at 28° C. Calculated number of colony forming units was normalized per centimeter of root length (total root length was determined based on images of root systems before their harvest). The experiment was conducted in three biological replicates, each with three technical replicates per condition, each sample consisted of five roots.

Results

After recognition of the beneficial impact of SA187 on plant physiology, the interaction of SA187 with plants was characterized in more detail to determine whether SA187 is able to efficiently colonize Arabidopsis as its non-native host. Therefore, its capacity to colonize Arabidopsis seedlings on ½ MS agar plates or in soil was analyzed by confocal microscopy. SA187 cells were stably transformed to express GFP (SA187-GFP), which did not affect their beneficial effect on Arabidopsis seedlings. Confocal microscopy revealed that SA187-GFP colonized both roots and shoots on ½ MS agar plates or in soil (data not shown). On vertical ½ MS agar plates, the first colonies (formed by a small number of cells) were observed on the root epidermis in the elongation zone, preferentially in grooves between epidermal cell files (data not shown). In the differentiation zone and older root parts, colonies were larger and proportional with the age of the region (data not shown). A similar colonization pattern was observed in soil-grown seedlings, however, with a more random distribution of colonies (data not shown). SA187-GFP colonies were also often found in cavities around the base of lateral roots (data not shown). While it was rare to detect SA187-GFP cells inside root tissues in 5-7 days old seedlings, the apoplast of the root cortex and even of the central cylinder was regularly occupied by small scattered colonies in 3 weeks old seedlings (data not shown). Indeed, in the initial plant assays, SA187 could be re-isolated from surface sterilized Arabidopsis roots, indicating that SA187 was proliferating inside root tissues. Inspecting shoots, SA187-GFP colonies were also found deep inside the apoplast of hypocotyls, cotyledons and the first true leaves, and in several cases bacterial cells were directly observed to penetrate through stomata of these organs (data not shown).

The colonization of root systems by SA187 (wild type strain) under normal and salt conditions was examined. Plants were germinated on ½ MS agar plates containing SA187 wild type strains, transferred to new ½ MS plates with or without 100 mM NaCl after 5 days, and parts of their root systems grown after the transfer were used for bacterial extraction after 5 more days. Interestingly, quantification based on counting of colony forming units (CFU) revealed that roots from salt conditions were twice more colonized than those from normal conditions, suggesting that in our experimental system plants can probably facilitate their accessibility to colonization by beneficial bacteria under stress conditions.

Example 5: SA187 Massively Reprograms Arabidopsis Gene Expression upon Colonization Methods RNAseq and qPCR Analysis Total RNA was extracted from 5-day-old plants either inoculated or not inoculated with SA187 and transferred for 10 more days on ½ MS plates with or without 100 mM NaCl using the Nucleospin RNA plant kit (Macherey-Nagel), including DNaseI treatment, and following manufacturer's recommendations.

RNA samples were analyzed by Illumina HiSeq deep sequencing (Illumina HiSeq 2000, Illumina). Three biological replicates were processed for each sample. Paired-end sequencing of RNA-seq samples was performed using Illumina GAIIx with a read length of 100 bp. Reads were quality-controlled using FASTQC (http://www.bioinformatics.babraham.ac.uk/projects/fastqc/). Trimmomatic was used for quality trimming (Bolger, et al., Bioinformatics, 30:2114-2120 (2014)). Parameters for read quality filtering were set as follows: Minimum length of 36 bp; Mean Phred quality score greater than 30; Leading and trailing bases removal with base quality below 3; Sliding window of 4:15. TopHat v2.0.9 (Trapnell, et al., Bioinformatics, 25:1105-1111 (2009)) was used for alignment of short reads to the A. thaliana genome TAIR10, Cufflinks v2.2.0 (Trapnell, et al., Nat Biotechnol, 28:511-515 (2010)) for transcript assembly and differential expression. To identify differentially expressed genes, specific parameters (p-value: 0.05; statistical correction: Benjamini Hochberg; FDR: 0.05) in cuffdiff were used. Post-processing and visualization of differential expression were done using cummeRbund v2.0.0 (Goff, et al., (2001)). Gene was considered as regulated if fold change $>\log_2^{10.61}$ and q-value $<0.05$ compared to Mock condition. RNAseq data set can be retrieved under NCBI geo submission ID GSE102950.

For qPCR analysis, mock and SA187-inoculated plants were used for RNA extraction as described above. Samples were used for analysis of either plant or SA187 gene expression. For bacteria alone, SA187 incubated for 4 h in liquid ½ MS or ½ MS with 100 mM NaCl at 28° C. and dark were used for RNA extraction, using the RiboPure™ RNA Purification Kit (Ambion), following manual instructions for Gram-negative bacteria, with the exception that no beads were added during bacterial lysis. RNA extraction was followed by DNAseI treatment.

cDNAs were synthetized using SuperscriptIII (Invitrogen): 1 μg of total RNA, oligo-dT as a primer, following manufacturer's recommendations. For Arabidopsis gene expression analyses, ACTIN2 (At3g18780) and UBIQUITIN10 (At4g05320) were used as reference genes. For SA187 gene expression analyses, infB, rpoB and gyrB were used as reference genes. All reactions were done in a CFX96 Touch™ Real-Time PCR Detection System (BIO-RAD) as follows: 50° C. for 2 min, 95° C. for 10 min; 40× [95° C. for 10 sec and 60° C. for 40 sec]; and a dissociation step to validate PCR products. All reactions were performed in three biological replicates, and each reaction as a technical triplicate. Gene expression levels were calculated using the Bio-Rad CFX manager software. Primer sequences used in this analysis are listed in Table 1 below.

TABLE 1

Primers Sequences Used.

| Primer name | Sequence (5' to 3') | Targetted gene | Purpose of the primer |
|---|---|---|---|
| 27F | AGAGTTTGATCCTGGCTCAG (SEQ ID NO: 14) | 16S rRNA | Bacterial strain identification |
| 1492R | TACGGYTACCTTGTTACGACTT (SEQ ID NO: 15) | | |
| P922-3G56400F1 | TGGTTCGTCCACGGAGAATG (SEQ ID NO: 16) | AT3G56400 | qPCR analysis |
| P923-3G56400R1 | CCCATTGACGTAACTGGCCT (SEQ ID NO: 17) | | |
| P854-1G01580F1 | GCAAGCGAAGCTGGAATCAG (SEQ ID NO: 18) | AT1G01580 | qPCR analysis |
| P855-1G01580R1 | AATCCCATTGCCGGTAGCAA (SEQ ID NO: 19) | | |
| P926-4G01250F1 | ACTAGCAAACCCAGTGGCTC (SEQ ID NO: 20) | AT4G01250 | qPCR analysis |
| P927-4G01250R1 | CATGCCCAGACATCGGAGTT (SEQ ID NO: 21) | | |
| P888-1G80440F2 | ATCGCTACGCCTGAATACCG (SEQ ID NO: 22) | AT1G80440 | qPCR analysis |
| P889-1G80440R2 | CCAGGAATCGGAGGAAGCTC (SEQ ID NO: 23) | | |

TABLE 1-continued

Primers Sequences Used.

| Primer name | Sequence (5' to 3') | Targetted gene | Purpose of the primer |
|---|---|---|---|
| P866-1G27730F1 | AGTCGAGCACTGGACAAAGG (SEQ ID NO: 24) | AT1G27730 | qPCR analysis |
| P867-1G27730R1 | TAGCTCAACTTCTCCACCGC (SEQ ID NO: 25) | | |
| P245-AT2G37870F1 | CTGTGCCAAAGTTGGTGCTC (SEQ ID NO: 26) | AT2G37870 | qPCR analysis |
| P246-AT2037870R1 | GTAACGTCCACATCGCTTGC (SEQ ID NO: 27) | | |
| P930-4G13420F1 | TACGTGGGGCCAAAGGATTC (SEQ ID NO: 28) | AT4G13420 | qPCR analysis |
| P931-4G13420R1 | CCCTCCTCCTCAGACATGA (SEQ ID NO: 29) | | |
| P309-AT3G30775F1 | CAACCCGTCTTCTCCGAACA (SEQ ID NO: 30) | AT3G30775 | qPCR analysis |
| P310-AT3G30775R1 | CGGTGCTTGTTGTCCAAAGG (SEQ ID NO: 31) | | |
| P237-AT3G53980F1 | CCGTCGGTTACAAGTGTGGA (SEQ ID NO: 32) | AT3G53980 | qPCR analysis |
| P238-AT3G53980R1 | AGGCCCAATGTTATCTCCTT CA (SEQ ID NO: 33) | | |
| P329-AT4G37800F1 | TTGGTTCGACCCTTCTCGTG (SEQ ID NO: 34) | AT4G37800 | qPCR analysis |
| P330-AT4G37800R1 | CCCTGATGGGCACATTGTCT (SEQ ID NO: 35) | | |
| P870-1G35140F1 | TGGATGCGAGAACGGACAAA (SEQ ID NO: 36) | AT1G35140 | qPCR analysis |
| P871-1G35140R1 | CATGGTCGATCTCCGGGAAG (SEQ ID NO: 37) | | |
| P281-AT2G39030F1 | GAGTCTGGTCTTGCCTCCAC (SEQ ID NO: 38) | AT2G39030 | qPCR analysis |
| P282-AT2G39030R1 | ATGCGTCTCAAGAAAGGGGG (SEQ ID NO: 39) | | |
| P962-5G51190F1 | CCAACGCAAACCACCTCTTG (SEQ ID NO: 40) | AT5G51190 | qPCR analysis |
| P963-5G51190R1 | CAGCCGCATACTTACCCCAT (SEQ ID NO: 41) | | |
| P862-1G13260F1 | GGTGTTTCTACGACGGGGTT (SEQ ID NO: 42) | AT1G13260 | qPCR analysis |
| P863-1G13260R1 | TTAGCTTCCCAACGTCGCTT (SEQ ID NO: 43) | | |
| P934-4G17490F1 | GGCGATTCTGAATTTCCCGC (SEQ ID NO: 44) | AT4G17490 | qPCR analysis |
| P935-4G17490R1 | TTGTACAGGCCACGACCATC (SEQ ID NO: 45) | | |
| P882-1G74930F1 | CTTTCGACGCCGCTCAATTT (SEQ ID NO: 46) | AT1G74930 | qPCR analysis |
| P883-1G74930R1 | GGAGGCGTCAACGACTTTTC (SEQ ID NO: 47) | | |
| P918-3G55980F1 | ATTGCAGACGTGTCGGTCCT (SEQ ID NO: 48) | AT3G55980 | qPCR analysis |
| P919-3G55980R1 | CAGCACAGTGAAGCGGAGTA (SEQ ID NO: 49) | | |

Hierarchical Clustering and Gene Family Enrichment

*Arabidopsis* regulated genes were used to generate HCL tree using Multi Experiment Viewer (MeV 4.9.0 version, TM4. Raw data were normalized for every gene. Hierarchical clustering was performed using Euclidian distances, average linkage and leaf order optimization.

Gene enrichment analyses were performed using AmiGO website.

Results

To uncover how salt stress tolerance is achieved in SA187-inoculated *Arabidopsis* seedlings, RNA-seq analysis was performed to compare the transcriptome of mock-inoculated to SA187-inoculated plants under non-saline (Mock and SA187), and salt stress conditions (Salt and SA187+Salt). Compared to mock conditions, 545, 3113 and 1822 genes were found to be differentially expressed in the "SA187", "Salt" and "SA187+Salt" samples, respectively. To obtain a global overview, the transcriptome data were organized by hierarchical clustering into 8 groups and analyzed for gene ontology enrichment (FIG. 4A-F).

Figures 5A, 5B, 5C:
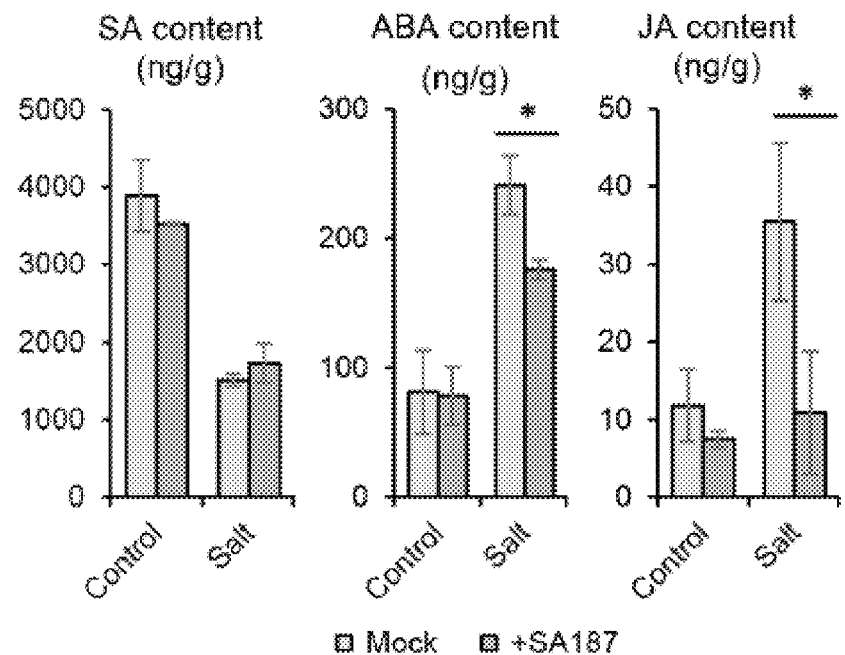
FIGS. 5A-5C are bar graphs showing (FIG. 5A) Salicylic acid (SA), (FIG. 5B) abscisic acid (ABA) and (FIG. 5C) jasmonic acid (JA) content of mock- and SA187-inoculated plants after growth on ½ MS with or without 100 mM NaCl (salt) for 12 days. Error bars indicate SE based on three biological replicates. Asterisks indicate a statistical difference based on Mann-Whitney test (* P<0.05).
Figures 5D, 5E, 5F:
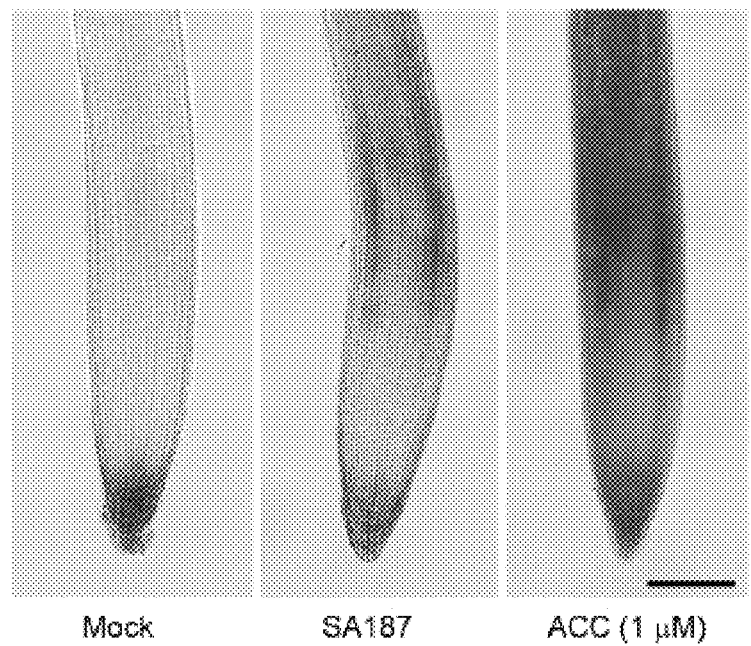
FIGS. 5D-5E are representative photos showing the ethylene reporter, pEBF2::GUS, in primary root tips of (FIG. 5D) mock- and (FIG. 5E) SA187-inoculated, and (FIG. 5F) ACC-treated 7-day-old seedlings under normal conditions (salt stress conditions provided similar results). Scale bar=100 μm.

Cluster 1 and 7 comprise the largest sets of differentially expressed genes with 1607 and 744 members, respectively, and consist of salt-stress regulated genes that were unaffected by the SA187 inoculation (FIG. 4B and 5F). Whereas Cluster 1 genes are strongly downregulated under salinity and are involved in water homeostasis, salicylic acid (SA) and defense response, those of Cluster 7 are highly upregulated and enriched in genes that are induced in response to water and salt stress or abscisic acid (ABA).

A specific effect of SA187 on the transcriptome of plants was found in Clusters 2, 3 and 4 (FIGS. 4C-E). Cluster 2 (354 genes) represents genes that are upregulated by SA187 independently of the growth conditions (FIG. 4C). This cluster was significantly enriched in plant defense genes such as chitin responsive genes but also in ethylene and jasmonic acid (JA) signaling (FIG. 4A-F). Importantly, Cluster 3 genes (246) are strongly downregulated in mock-inoculated plants under salt stress conditions but remain unaltered upon SA187-inoculation (FIG. 4D). These genes have a role in the primary metabolism, such as photosynthesis, carbon and energy metabolisms. On the contrary, Cluster 4 genes (464) are enriched in ABA and abiotic stress response and are upregulated in salt-treated plants, but not when the plants were inoculated with SA187 (FIG. 4E).

In summary, these data indicate that SA187 colonization triggers in *Arabidopsis* the expression of genes involved in defense response as shown by the significant enrichment for chitin responsive genes and ethylene and JA signaling. Moreover, under saline conditions, SA187-inoculated plants release themselves from the impact of abiotic stress (ABA), maintain higher metabolic and photosynthetic activity, and can therefore grow better than mock-inoculated plants.

Example 6: SA187 Modulates Abscisic Acid, Jasmonic Acid, and Ethylene Hormonal Pathways Under Salt Stress Methods Hormone Content Analysis For each sample, 10 mg of freeze-dried powder were extracted with 0.8 mL of acetone/water/acetic acid (80/19/1 v:v:v). For each sample, 2 ng of each standard was added to the sample: abscisic acid, salicylic acid, jasmonic acid, and indole-3-acetic acid stable labeled isotopes used as internal standards were prepared as described previously (Le Roux, et al., *PLoS One*, 9:e99343 (2014)). The extract was vigorously shaken for 1 min, sonicated for 1 min at 25 Hz, shaken for 10 minutes at 4° C. in a Thermomixer (Eppendorf), and then centrifuged (8000 g, 4° C., 10 min). The supernatants were collected, and the pellets were re-extracted twice with 0.4 mL of the same extraction solution, then vigorously shaken (1 min) and sonicated (1 min; 25 Hz). After the centrifugations, three supernatants were pooled and dried.

Each dry extract was dissolved in 140 µL of acetonitrile/water (50/50; v/v), filtered, and analyzed using a Waters Acquity ultra performance liquid chromatograph coupled to a Waters Xevo Triple quadrupole mass spectrometer TQS (UPLC-ESI-MS/MS). The compounds were separated on a reverse-phase column (Uptisphere C18 UP3HDO, 100×2.1 mm, 3 pm particle size; Interchim, France) using a flow rate of 0.4 mL·min$^{-1}$ and a binary gradient: (A) acetic acid 0.1% in water (v/v) and (B) acetonitrile with 0.1% acetic acid. For ABA, salicylic acid, jasmonic acid, the following binary gradients were used (time, % A): (0 min, 98%), (3 min, 70%), (7.5 min, 50%), (8.5 min, 5%), (9.6 min, 0%), (13.2 min, 98%), (15.7 min, 98%), and the column temperature was 40° C. Mass spectrometry was conducted in electrospray and Multiple Reaction Monitoring scanning mode (MRM mode), in the negative ion mode. Relevant instrumental parameters were set as follows: capillary 1.5 kV (negative mode), source block and desolvation gas temperatures 130° C. and 500° C., respectively. Nitrogen was used to assist the cone and desolvation (150 L·h$^{-1}$ and 800 L·h$^{-1}$, respectively), argon was used as the collision gas at a flow of 0.18 mL·min$^{-1}$. Samples were reconstituted in 140 µL, of 50/50 acetonitrile/H$_2$O (v/v) per mL of injected volume. The limit of detection (LOD) and limit of quantification (LOQ) were extrapolated for each hormone from calibration curves and samples using Quantify module of MassLynx software, version 4.1.

GUS Staining

Seedlings were vacuum infiltrated with the pre-fixation buffer [0.3% formaldehyde, 0.28% mannitol, 50 mM sodium phosphate buffer (pH 7.2)], washed with phosphate buffer and incubated in staining solution [250 µM K$_3$Fe(CN)$_6$, 250 µM K$_4$Fe(CN)$_6$, 2% Triton-X, 1 mM 5-bromo-4-chloro-3-indolyl-b-D-glucuronic acid (X-GlcA; Duchefa), 50 mM sodium phosphate buffer (pH 7.2)]. Tissue was cleared with Visokol (Phytosys) overnight and observed with Axio Imager 2 (Zeiss) equipped with Plan-Neofluar 10×/0.45 objective.

Results

Since the transcriptome analysis indicated possible roles of several hormone pathways in the SA187-induced growth promotion under salt stress, the levels of salicylic acid (SA), jasmonic acid (JA) and abscisic acid (ABA) were measured in mock- and SA187-inoculated plants. SA187 did not significantly change plant SA levels in the absence or presence of salt (FIG. 5A). Plant ABA and JA concentrations also remained unchanged upon SA187 colonization under normal conditions, but their salt-induced accumulation was significantly lower in SA187-inoculated plants (FIG. 5B-C), indicating a partial attenuation of stress responses in these plants.

To assess the level of ethylene in *Arabidopsis* roots and possibly confirm the activation of the ethylene signaling pathway observed in Cluster 2, the ethylene-dependent pEBF2::GUS reporter was used (Konishi, et al., *Plant J*, 55:821-831 (2008)). In contrast to mock-inoculated seedlings (FIG. 5D), the reporter line showed strong GUS activity in root tips upon SA187-inoculation (FIG. 5E), similar to the treatment with the ethylene precursor amino-cyclopropane-1-carboxylic acid (ACC) (FIG. 5F), indicating the activation of the ethylene signaling pathway.

Example 7: Ethylene Perception Mutants are Compromised in the Beneficial Response to SA187

To substantiate the phytohormone quantifications, *Arabidopsis* hormone deficient or insensitive mutants were analyzed. The JA-receptor coi1-1 mutant (Xie, et al., *Science*, 280:1091-1094 (1998)), JA-insensitive jar1-1 (Staswick, et al., *Proc Natl Acad Sci USA*, 89:6837-6840 (1992)), the ABA biosynthesis aba2-1 mutant (Schwartz, et al., *Plant Physiol*, 114:161-166 (2997)), or the ABA receptor quadruple pyr1-1pyl1-1pyl2-1pyl4-1 mutant (Park et al., *Science*, 324:1068-1071 (2009)) maintained the SA187 beneficial activity upon salt stress, indicating that ABA or JA may not play a major role in this interaction (FIG. 6A-B).

However, the ethylene insensitive ein2-1 and ein3-1 mutants (Guzmán, et al., *Plant Cell*, 2:513-523 (1990); Roman, et al., *Genetics*, 139:1391-1409 (1995)), impaired in ethylene perception, were strongly compromised in the beneficial effect of SA187, indicating that ethylene sensing could be of importance in SA187-induced tolerance of *Arabidopsis* to salt stress conditions. This result was confirmed by the up-regulation of the four ethylene-induced genes, ERF105 (FIG. 6D), ERF018 (FIG. 6F), RAV1 (FIG. 6E) and SZF1 (FIG. 6G), upon colonization by SA187. Moreover, application of 100 nM ACC during salt stress could largely mimic the beneficial activity of SA187 on plants (FIG. 6C).

Figure 6A:
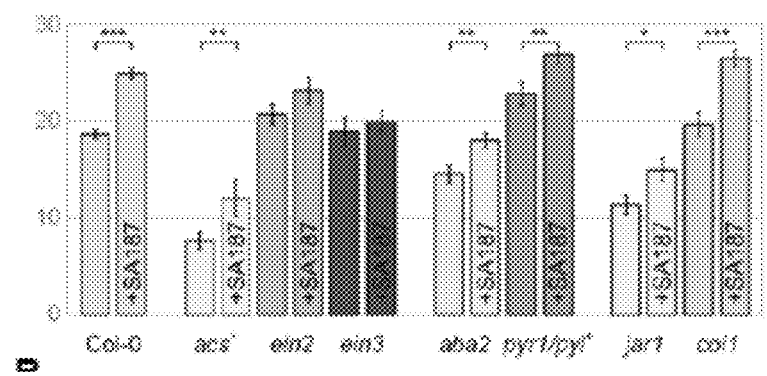
FIGS. 6A and 6B are bar graphs showing (FIG. 6A) the fresh weight (mg) and (FIG. 6B) beneficial index (fresh weight ratio between SA187-colonized and control seedlings) of mock- or SA187-inoculated mutants in hormonal pathways transferred to ½ MS+100 mM NaCl for 12 days. acs=heptuple mutant acsl-1 acs2-1 acs4-1 acsS-2 acs6-1 acsl-1 acs9-1, and pyrl/py1=quadruple mutant pyrl py/1 py/2 py/4. All plots represent the mean of three biological replicates (n>36).
Figure 6B:
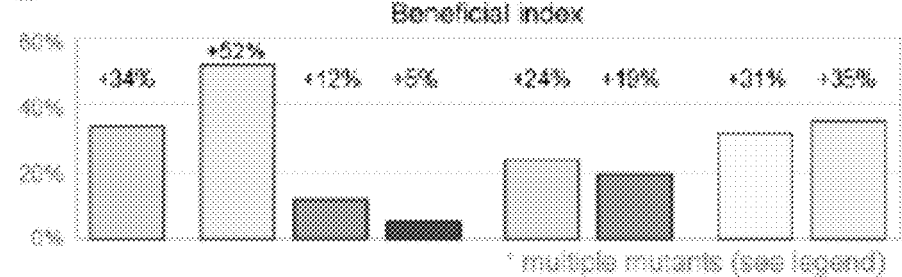
Figure 6C:
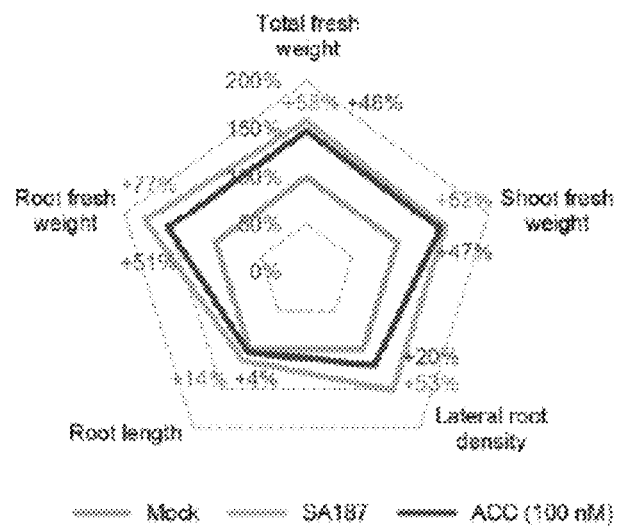
FIG. 6C is a graph showing *Arabidopsis* growth parameters under salt stress. 100 nM ACC partially mimics the effect of SA187 on salt stress tolerance improvement in *Arabidopsis* seedlings. Five-day-old-seedlings were transferred to ½ MS+100 mM NaCl with or without ACC and evaluated after 12 additional days. SA187-inoculated plants were used for comparison.
Figure 6D:
FIGS. 6D-6G are bar graphs showing qPCR expression analysis of four ethylene-associated genes, (FIG. 6D) ERF105 (At5g51190), (FIG. 6E) RAV1 (At1g13260), (FIG. 6F) ERF018 (At1g74930), and (FIG. 6G) SZF1 (At3g55980), in 17-day-old mock- (gray bar) and SA187- (green bar) inoculated *Arabidopsis* seedlings exposed for 12 days to ½ MS with or without 100 mM NaCl. Normalized expression indicates the linear fold change compared to mock-treated plants on ½ MS. Values represent means of three biological experiments, each in three technical replicates. Error bars indicate SE.
Figure 6E:
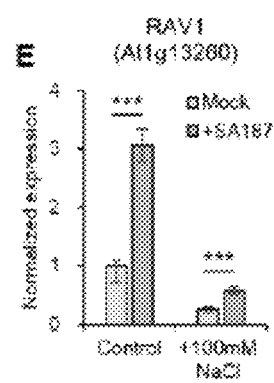
Figure 6F:
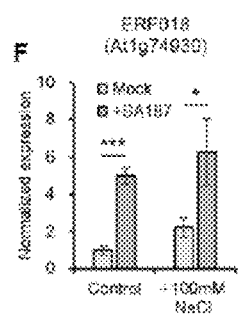
Figure 6G:
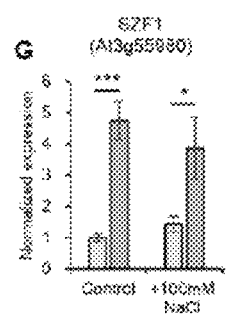
Figure 6H:
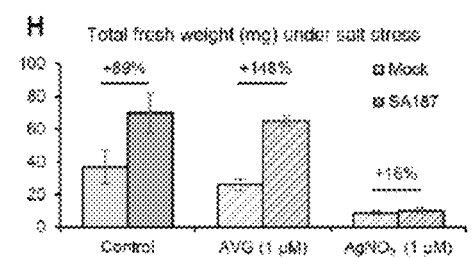
FIG. 6H is a bar graph showing total fresh weight of mock- (gray bars) and SA187- (green bars) inoculated 18-day-old *Arabidopsis* seedlings on ½ MS with 100 mM NaCl supplemented with the ethylene synthesis inhibitor AVG (1 μm) or ethylene signaling inhibitor AgN03 (1 μm). Error bars representing SE and beneficial index(%) are displayed. Asterisks indicate a statistical difference based on Student t-test (* P<0.05;  P<0.01; * P<0.001).

In contrast, the heptuple ethylene-biosynthesis deficient mutant acs1-1 acs2-1 acs4-1 acs5-2 acs6-1 acs7-1 acs9-1 (called acs in this study) still showed full sensitivity to the beneficial activity of SA187 under salt stress (FIG. 6A). Additionally, the SA187 beneficial effect was maintained when plants were treated with amino-ethoxy-vinyl glycine (AVG, 1 µM), an ethylene production inhibitor blocking ACC synthesis (Schaller, et, al., in: Ethylene Signaling Methods and Biosynthesis, pp 233-235 (2017)) (FIG. 6H). However, when plants were treated with silver nitrate (AgNO$_3$, 1 µM), which interferes with ethylene perception (Schaller, et al., in: Ethylene Signaling Methods and Biosynthesis, pp 233-235 (2017)), inoculated plants did not exhibit any SA187-induced tolerance to salt stress (FIG. 6H).

Altogether, these results indicate that the beneficial effect of SA187 may not be mediated by JA perception or the ABA pathway, but rather by ethylene perception, as it was found to be necessary for SA187-induced salt stress tolerance on *Arabidopsis* plants.

Example 8: *Arabidopsis* Upregulates the Methionine Salvage Pathway in SA187

Methods

Measurement of In Vitro Ethylene Emanation

A fresh SA187 culture was prepared by inoculation of 50 mL of liquid LB medium with 1 mL of overnight-grown culture. Subsequently, 2 mL of fresh culture was transferred to 10 mL chromatography vials and sealed with a rubber plug and snap-cap (Chromacol) after 0, 1, 2 or 4 hours of growth on a shaker incubator (220 rpm, 28° C.). The sealed vials were again transferred to the shaker incubator for another 2 hours to allow ethylene accumulation. Three biological replicates were prepared at each time point along with 3 controls to correct for background ethylene emanation. Ethylene emission was measured with a laser-based photo-acoustic detector (ETD-300 ethylene detector, Sensor Sense, The Netherlands) (van de Poel, et al., *Methods in Molecular Biology: Ethylene Signaling, Methods and Protocols*, 2017). Immediately after the ethylene measurement, OD$_{600}$ was determined with Implen NanoPhotometer NP80 (Sopachem Life Sciences, Belgium) to correct for the total amount of bacterial cells present in the samples.

Results

Figures 7A, 7B:
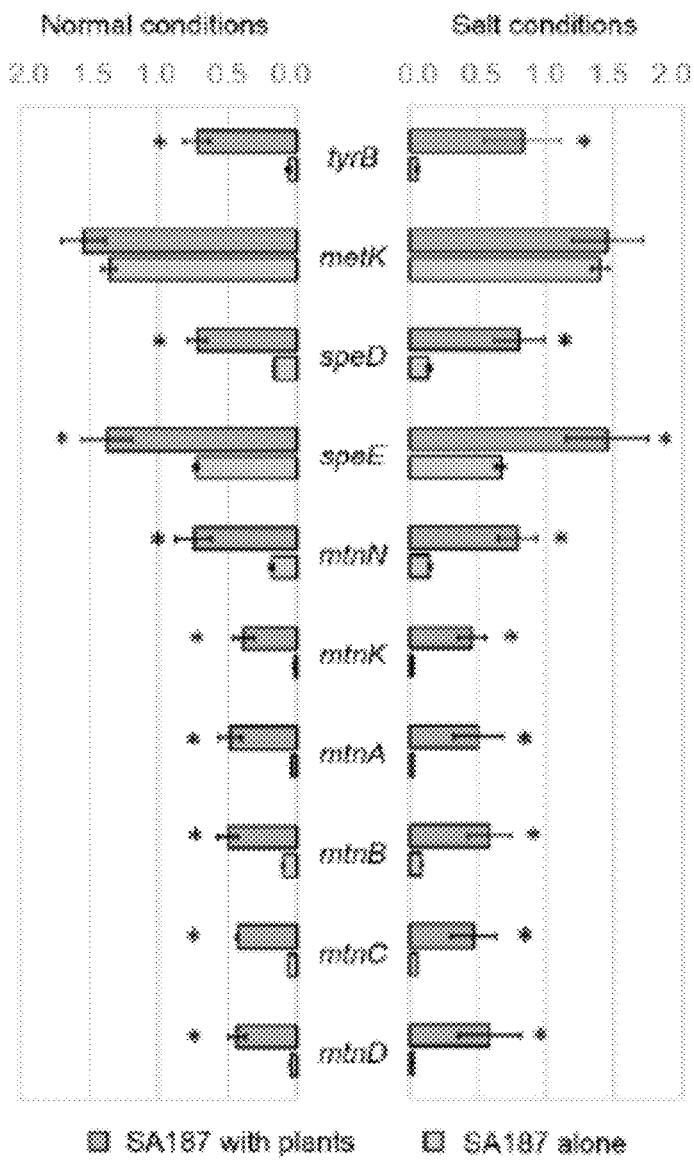
FIGS. 7A and 7B are bar graphs showing qPCR analysis of the methionine salvage cycle gene expression of SA187 colonizing plants in (FIG. 7A) control or (FIG. 7B) salt stress conditions compared to SA187 alone in ½ MS with or without 100 mM NaCl. Values represent means of three biological experiments, each in three technical replicates. Error bars indicate SE.

The previous results suggested that ethylene most likely originates from SA187 cells rather than from the canonical plant ACC synthase (ACS) pathway. To support the hypothesis that SA187 provides ethylene to promote plant growth, the genome of SA187 was searched for bacterial genes encoding ACS or ethylene forming enzymes (EFE). No ACS- or EFE-related genes were found in SA187, but the methionine salvage pathway is conserved in SA187, and one of its components, KMBA, is known to be an ethylene precursor (Eckert, et al., *Biotechnol Biofuels,* 7:33 (2014)). While SA187 alone did not produce ethylene when grown on synthetic media, the expression level of most of the genes encoding the KMBA pathway were upregulated in SA187 upon plant colonization compared with bacteria incubated for 4 h in liquid ½ MS with or without 100 mM NaCl in the absence of plants (FIG. 7A-B).

Figure 7C:
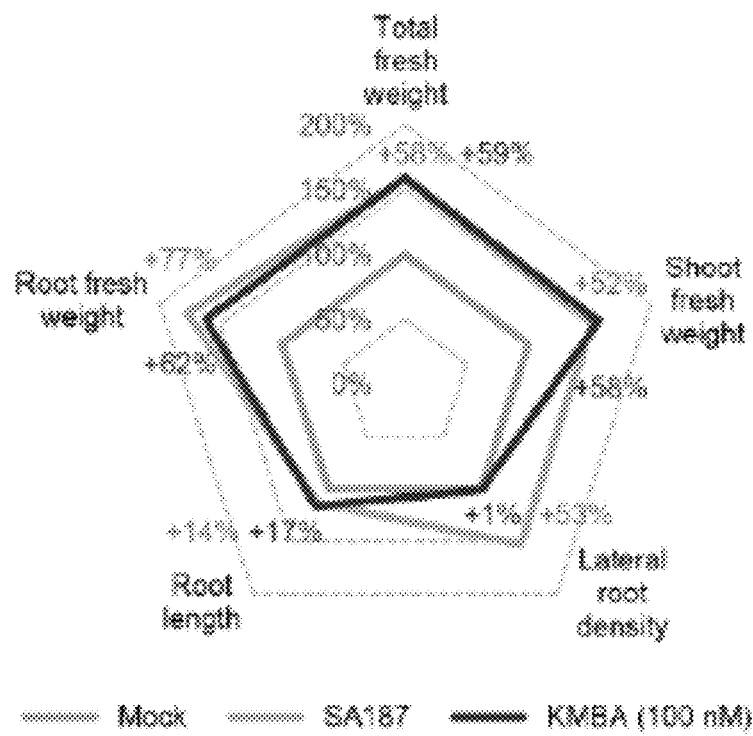
FIG. 7C is a graph showing *Arabidopsis* growth parameters under salt stress. Mock plants were transferred 5 days after germination to ½ MS+100 mM NaCl with or without KMBA and evaluated after 12 additional days. SA187-inoculated plants transferred to ½ MS+100 mM NaCl were used as a positive control.

To confirm that KMBA could function as an ethylene precursor during the beneficial plant-microbe interaction, the effect of KMBA on *Arabidopsis* in comparison to SA187 inoculation was tested. Under salt stress conditions, application of 100 nM KMBA induced a similar beneficial activity on *Arabidopsis* as SA187 with a similar increase in both root and shoot fresh weight (FIG. 7C).

Figure 7D:
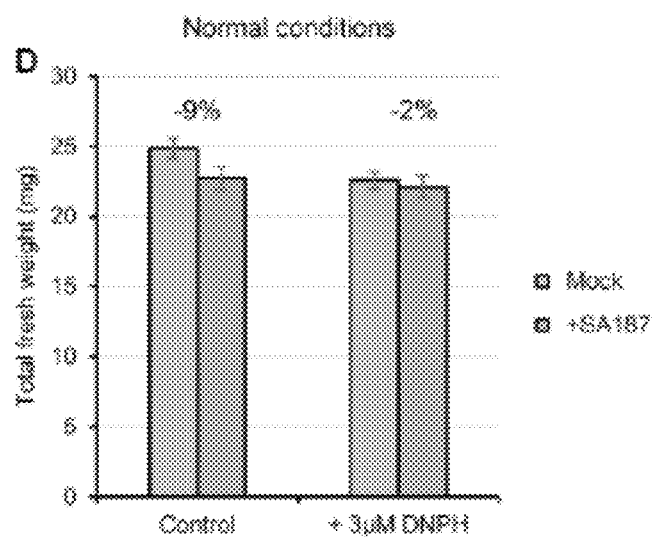

2,4-dinitrophenylhydrazine (DNPH) is a known interactor of KMBA in vitro that was previously shown to precipitate *Botrytis cinerea* produced KMBA and consequently impair the production of ethylene by photo-oxidation (Chague, et al., *FEMS Microbiol Ecol,* 40:143-149 (2002)). When plants were cultivated with 3 µM DNPH, SA187-induced salt tolerance was greatly reduced from 68% to 14% (FIG. 7D-E), showing the importance of KMBA in mediating SA187-induced plant tolerance to salt stress.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10524471B2). An electronic copy of the "Sequence Listing" will also be available from the USPTO upon request and payment of the fee set forth in 37 CFR 1.19(b)(3).

We claim:

1. A method for increasing salt tolerance in a plant comprising: treating a plant grown under salt stress with an amount of 2-keto-4-methylthiobutyric acid effective to increase salt tolerance in the plant relative to an untreated plant.

2. The method of claim 1, wherein the amount of 2-keto-4-methylthiobutyric acid is in solution.

3. The method of claim 1, wherein the solution is an aqueous solution.

4. The method of claim 1, wherein the amount of 2-keto-4-methylthiobutyric acid is in water.

5. The method of claim 2, wherein the solution comprises 1.0 to 10% salt, optionally, wherein the salt is selected from the group consisting of salts of sodium, chloride, sulfate, magnesium, calcium, potassium, and combinations thereof.

6. The method of claim 5, wherein the solution comprises 3.5% salt.

7. The method of claim 1, wherein the salt stress is provided by growing the plant under conditions selected from the group consisting of sodic soil and aqueous saline solution, and combinations thereof.

8. The method of claim 1, wherein the 2-keto-4-methylthiobutyric acid is present at a concentration of 1.0 to 250 nM.

9. The method of claim 8, wherein the 2-keto-4-methylthiobutyric acid is present at a concentration of at least 100 nM.

10. The method of claim 7, comprising growing a seed or the plant in a plant substrate, wherein the plant substrate comprises an effective amount of SA187 to colonize the seed or a root of the plant to provide abiotic stress resistance to the seed or plant.

11. A method of increasing salt tolerance in a plant comprising treating the plant with a composition comprising an amount of 2-keto-4-methylthiobutyric acid effective to increase salt tolerance in the plant relative to an untreated plant, wherein the 2-keto-4-methylthiobutyric acid is in salt water.

12. The method of claim 11, further comprising inoculating the plant with a microbial system to produce 2-keto-4-methylthiobutyric in the plant.

13. The method of claim 12, wherein the microbial system comprises an effective amount of SA187 to colonize plant seed or a root of the plant to provide abiotic stress resistance to the seed or plant;

or a bacterium genetically engineered to overexpress express L-amino acid deaminase (L-AAD) from Proteus vulgaris or one or more genes from the methionine salvage pathway selected from the group consisting of mtnN (EC 3.2.2.16), tyrB encoding a wide spectrum aminotransferase, mtnA, encoding MtnA (methylthioribose-1-phosphate isomerase), mtnB, encoding a methylthioribulose-1-phosphate dehydratase; mtnC, encoding an enolase-phosphatase, mtnD (ykrZ), encodiong an aci-reductone dioxygenase; mtnK, encoding a methylthioribose kinase; metK, enclodig S-adenosylmethionine (SAM) synthetase; speE encoding a spermidine synthetase; and speD, encoding an S-adenosylmethionine decarboxylase.

14. The method of claim 11, wherein the plant is a forage crop.

15. The method of claim 11, wherein salt tolerance is determined by fresh weight of seedling shoots, seedling roots, and/or dry weight of seedlings.

16. The method of claim 11, wherein the composition comprises 1.0 to 10% salt solution.

17. A method for cultivating a plant comprising:
planting seeds or seedlings of the plant; and
irrigating the seeds or seedlings with a saline solution comprising 2-keto-4-methylthiobutyric acid.

18. The method of claim 17, wherein the plant is selected from the group consisting of rice, wheat, sugarcane, maize, soybean, cotton, vegetables, rape, mustard, sorghum, millet, grass, Brassica spp., rapeseed, barley, hay, and alfalfa.

19. An agricultural irrigation solution comprising: 1.0 to 250 nM 2-keto-4-methylthiobutyric acid in an aqueous saline solution.

20. The solution of claim 19, wherein the aqueous saline solution comprises at least 3% salt.

21. The irrigation solution-of claim 19, wherein the aqueous saline solution comprises 1 to 10% salt.

22. A method of for increasing salt tolerance in a plant comprising growing the plant in a plant substrate comprising the irrigation solution of claim 19.

23. The method of claim 22, wherein the plant substrate is selected from the group consisting of soil, peat, compost, vermiculite, perlite, sand, and clay, and combinations thereof.

24. The solution of claim 19, in a plant substrate selected from the group consisting of soil, peat, compost, vermiculite, perlite, sand, and clay, and combinations thereof.

25. An agricultural composition comprising:
2-keto-4-methylthiobutyric acid in an aqueous saline solution and plant seeds, plant seedlings or mature plants, wherein the 2-keto-4-methylthiobutyric acid is
in an effective amount to increase salt tolerance in the plant seeds, plant seedlings or mature plants relative to untreated plant seeds, plant seedlings or mature plant.

26. The composition of claim 25, comprising the 2-keto-4-methylthiobutyric acid in an aqueous saline solution, and plant seeds, plant seedlings or mature plants.

* * * * *